(12) United States Patent
Machacek et al.

(10) Patent No.: US 10,947,234 B2
(45) Date of Patent: Mar. 16, 2021

(54) PRMT5 INHIBITORS

(71) Applicant: Merck Sharp & Dohme Corp., Rahway, NJ (US)

(72) Inventors: Michelle R. Machacek, Belmont, MA (US); David J. Witter, Norfolk, MA (US); Michael Hale Reutershan, Brighton, MA (US); Michael D. Altman, Newton, MA (US); Paul Anthony Stupple, Victoria (AU)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/762,201

(22) PCT Filed: Nov. 5, 2018

(86) PCT No.: PCT/US2018/059130
§ 371 (c)(1),
(2) Date: May 7, 2020

(87) PCT Pub. No.: WO2019/094311
PCT Pub. Date: May 16, 2019

(65) Prior Publication Data
US 2020/0361931 A1    Nov. 19, 2020

Related U.S. Application Data

(60) Provisional application No. 62/583,250, filed on Nov. 8, 2017.

(51) Int. Cl.
*C07D 471/04*    (2006.01)
(52) U.S. Cl.
CPC ................. *C07D 471/04* (2013.01)

(58) Field of Classification Search
CPC ................................................ C07D 471/04
USPC ............................................... 514/300
See application file for complete search history.

(56) References Cited

U.S. PATENT DOCUMENTS

2017/0298075 A1 * 10/2017 Bergman ............ C07D 239/42

FOREIGN PATENT DOCUMENTS

WO    2012118850 A1    9/2012

* cited by examiner

*Primary Examiner* — Rita J Desai
(74) *Attorney, Agent, or Firm* — Sarah L. Hooson; Catherine D. Fitch

(57) ABSTRACT

The present invention provides a compound of Formula (I) or the pharmaceutically acceptable salts thereof, which are PRMT5 inhibitors.

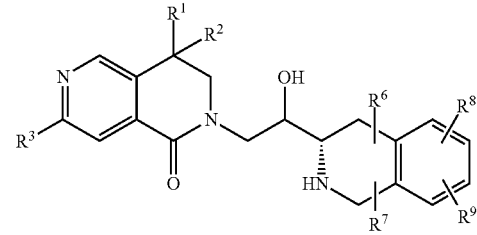

9 Claims, No Drawings

PRMT5 INHIBITORS

CROSS-REFERENCE TO RELATED APPLICATIONS

This application is a U.S. National Phase application under 35 U.S.C. § 371 of PCT/US2018/059130 filed on Nov. 5, 2018, which claims priority to U.S. 62/583,250 filed on Nov. 8, 2017, the contents of which are hereby incorporated by reference in their entireties.

BACKGROUND OF THE INVENTION

PRMT5 (aka JBP1, SKB1, 1BP72, SKB1his and HRM-TIL5) is a Type II arginine methyltransferase, and was first identified in a two-hybrid search for proteins interacting with the Janus tyrosine kinase (Jak2) (Pollack et al., 1999). PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodelling components BRG1 and BRM.

PRMT5 is involved in the methylation and functional modulation of the tumor suppressor protein p53. (See Berger, 2008; Durant et al., 2009; Jansson et al., 2008; Scoumanne et al., 2009). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumor suppression.

The role of PRMT5 and p53 arginine methylation on cell cycle regulation and DNA damage response have been explored by both Jansson et al. and Scoumanne et al. (Jansson et al., 2008; Scoumanne et al., 2009). Although some differences are evident between the results from the two groups concerning cell cycle regulation in unperturbed cells (which may be ascribed to cell type specific effects and/or the actual nature of the experimental arrangements), both groups report similar results with respect to the DNA damage response.

In response to DNA damage caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, but not PUMA, NOXA, AlP1 & APAF1, p53 target genes linked to apoptosis.

Knockdown of PRMT5 (but not PRMT1 or CARM1/PRMT4) results in decreased p53 stabilisation, decreased basal p53 levels, decreased p53 oligomerisation, and also decreased expression of eIF4E a major component of translational machinery involved in ribosome binding to mRNA. Indeed, elF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al. showed that a p53 mutant in which each of the three critical arginine residues were substituted with lysine (p53KKK) retained the ability to induce apoptosis but its cell cycle arrest activity was significantly compromised.

Moreover, pS3KKK also has a significantly reduced ability to induce transcription of p21, by contrast with APAF1. The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

PRMT5 is aberrantly expressed in around half of human cancer cases, further linking this mechanism to cancers. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including chronic lymphcytic leukemia (CLL) are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+ B lymphocytes (Pal et al., 2007; Wang et al., 2008). Intriguingly, despite elevated levels of PRMT5 protein in these tumor cells, the levels of PRMT5 mRNA are reduced (by a factor of 2-5). Translation of PRMT5 mRNA is, however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumor suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

Hemoglobin is a major protein in red blood cells and is essential for the transport of oxygen from the lungs to the tissues. In adult humans, the most common hemoglobin type is a tetramer called hemoglobin A, consisting of two α and two β subunits. In human infants, the hemoglobin molecule is made up of two α and two Y chains. The gamma chains are gradually replaced by subunits as the infant grows. The developmental switch in human ß-like globin gene subtype from foetal (Y) to adult (ß) that begins at birth heralds the onset of the hemoglobinopathies ß-thalassemia and sickle cell disease (SCD). In ß-thalassemia the adult chains are not produced. In SCD a point mutation in the coding sequence in the ß globin gene leads to the production of a protein with altered polymerisation properties. The observation that increased adult Y-globin gene expression (in the setting of hereditary persistence of foetal hemoglobin (HPFH) mutations) significantly ameliorates the clinical severity of ß-thalassemia and SCD has prompted the search for therapeutic strategies to reverse Y-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the Y-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of Y-gene expression, and complete abrogation of DNA methylation at the Y-promoter. Treatment of human erythroid progenitors with non-specific methyltransferase inhibitors (Adox and MTA) also resulted in upregulation of Y-gene expression (He Y, 2013). Inhibitors of PRMT5 thus have potential as therapeutics for hemoglobinopathies such as ß-thalassemia and Sickle Cell Disease (SCD).

The present inventors have developed particular tetrahydroisoquinolines that inhibit the activity of PRMT5 and therefore may be of use in treating conditions ameliorated by the inhibition of the activity of PRMT5.

SUMMARY OF THE INVENTION

Compounds of Formula I

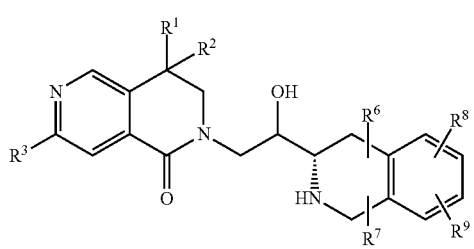

or the pharmaceutically acceptable salts, esters, and prodrugs thereof, which are PRMT5 inhibitors. Also provided are pharmaceutical compositions comprising compounds of Formula I, and methods of using these compounds to treat cancer.

DETAILED DESCRIPTION OF THE INVENTION

Compounds of Formula I

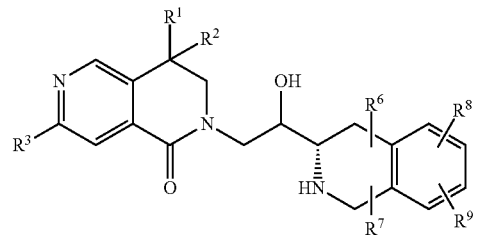

or pharmaceutically acceptable salts thereof, wherein
$R^1$ is hydrogen or $C_{1-4}$ alkyl, and
$R^2$ is hydrogen or $C_{1-4}$ alkyl, or
$R^1$ and $R^2$, together with the atom to which they are attached, form a $C_{3-6}$ cycloalkyl ring;
$R^3$ is halogen or —$NHR^4$;
$R^4$ is a 5- or 6-membered saturated heterocycle;
$R^5$ is $C_{1-4}$ alkyl; and
$R^6$, $R^7$, $R^8$, and $R^9$, are independently selected from hydrogen, halogen and $C_{1-4}$ alkyl.

In an embodiment of the invention,
$R^1$ is hydrogen or $C_{1-4}$ alkyl, and
$R^2$ is hydrogen or $C_{1-4}$ alkyl, or
$R^1$ and $R^2$, together with the atom to which they are attached, form a $C_{3-6}$ cycloalkyl ring;
$R^3$ is halogen or —$NHR^4$;
$R^4$ is a 5- or 6-membered saturated heterocycle containing 1 N atom, wherein the heterocycle is unsubstituted or substituted with one, two, or three moieties independently selected from the group consisting of $C(O)R^5$ and halogen;
$R^5$ is $C_{1-4}$ alkyl; and
$R^6$, $R^7$, $R^8$, and $R^9$, are independently selected from hydrogen, halogen and $C_{1-4}$ alkyl.

In an embodiment of the invention,
$R^1$ is hydrogen or $C_{1-4}$ alkyl;
$R^2$ is hydrogen or $C_{1-4}$ alkyl;
$R^3$ is halogen or —$NHR^4$;
$R^4$ is a 6-membered saturated heterocycle containing 1 N atom, wherein the heterocycle is unsubstituted or substituted with $C(O)R^5$;
$R^5$ is $C_{1-4}$ alkyl; and
$R^6$, $R^7$, $R^8$, and $R^9$, are hydrogen.

In an embodiment of the invention, $R^1$ is $CH_3$ or $CH_2CH_3$.

In an embodiment of the invention, $R^2$ is hydrogen or $CH_3$.

In an embodiment of the invention, $R^3$ is

Cl, or

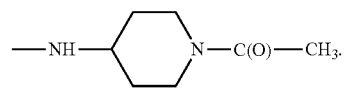

In an embodiment of the invention, the compound is

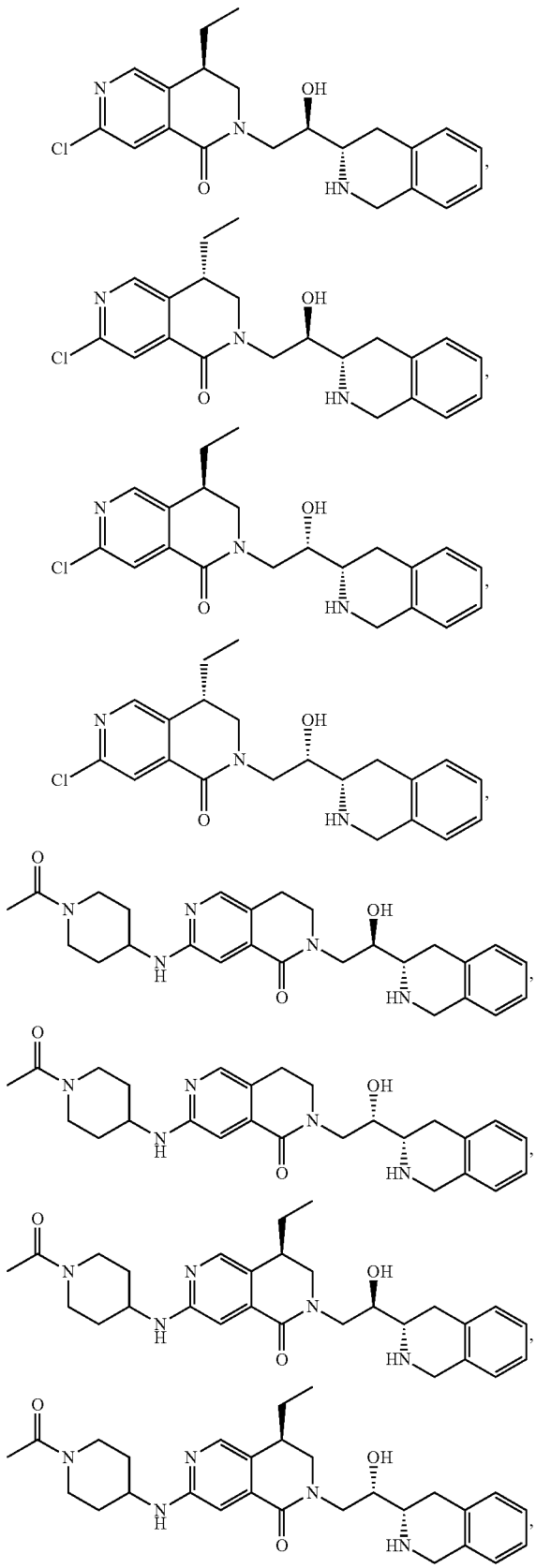

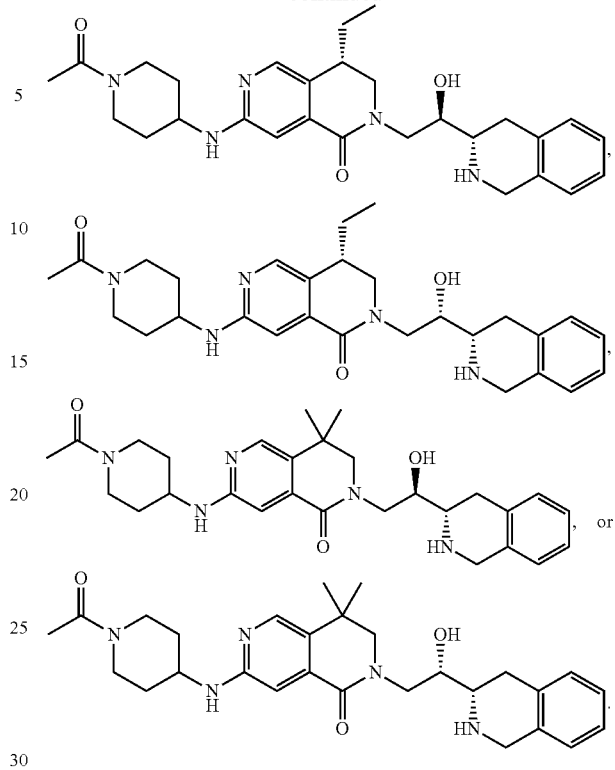

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient) for treating cancer. The term "antineoplastic agent" means a drug (medicament or pharmaceutically active ingredient) for treating cancer (i.e., a chemotherapeutic agent). The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "compound" with reference to the antineoplastic agents, includes the agents that are antibodies. The term "consecutively" means one following the other. The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the PRMT5 inhibitor (i.e., a compound of the invention) is that amount which results in the reduction in PRMT5 activity. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The invention also provides a pharmaceutical composition comprising an effective amount of at least one compound of Formula I and a pharmaceutically acceptable carrier. The invention also provides a pharmaceutical composition comprising an effective amount of at least one compound of Formula I and an effective amount of at least one other pharmaceutically active ingredient (such as, for example, a chemotherapeutic agent), and a pharmaceutically acceptable carrier.

The invention also provides a method of inhibiting PRMT5 in a patient in need of such treatment comprising administering to said patient an effective amount of at least one compound of Formula I. The invention also provides a method for treating cancer in a patient in need of such treatment, said method comprising administering to said patient an effective amount of at least one compound of Formula I. The invention also provides a method for treating cancer in a patient in need of such treatment, said method comprising administering to said patient an effective amount of at least one compound of Formula I, in combination with an effective amount of at least one chemotherapeutic agent. The methods of the invention include the administration of a pharmaceutical composition comprising at least one compound of the invention and a pharmaceutically acceptable carrier. The invention also provides any of the above methods of treating cancer wherein the cancer is colorectal. The invention also provides any of the above methods of treating cancer wherein the cancer is melanoma. The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of the invention is directed to a method of treating cancer in a patient in need of such treatment, said method comprising administering an effective amount of a compound of Formula I. Another example of the invention is directed to a method of treating cancer in a patient in need of such treatment, said method comprising administering to said patient an effective amount of a compound of Formula I, and an effective amount of at least one chemotherapeutic agent.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians'Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), the Physicians' Desk Reference, 60$^{th}$ Edition, 2006 (published by Thompson PDR, Montvale, N.J. 07645-1742), and the Physicians' Desk Reference, 64$^{th}$ Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of Formula I, or a pharmaceutically acceptable salt thereof, to said patient. Another example of the invention is directed to a method of treating colo-rectal cancer in a patient in need of such treatment, said method comprising administering to said patient an effective amount of a compound of Formula I, or a pharmaceutically acceptable salt thereof, and an effective amount of at least one chemotherapeutic agent.

In one example of the invention the cancer treated is melanoma. Thus, another example of the invention is directed to a method of treating melanoma in a patient in need of such treatment, said method comprising administering an effective amount of a compound of Formula I, or a pharmaceutically acceptable salt thereof, to said patient. Another example of the invention is directed to a method of treating melanoma in a patient in need of such treatment, said method comprising administering to said patient an effective amount of a compound of Formula I, or a pharmaceutically acceptable salt thereof, and an effective amount of at least one chemotherapeutic agent.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

PD-1 inhibitors include pembrolizumab (lambrolizumab), nivolumab and MPDL3280A. PD-L1 inhibitors include atezolizumab, avelumab, and durvalumab.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13 (9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2 (diethylamino)ethylamino]-7-methoxy-9-oxo-9H-thioxanthen-4-ylmethyl]formamide, N-(2-(dimethylamino)ethyl) acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680 (tozasertib).

"Antiproliferative agents" includes antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and rosuvastatin (CRESTOR® U.S. Reissue Pat. RE37,314) cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, and 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib, etoricoxib, and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. No. 60/310,927 (filed Aug. 8, 2001) and Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of the specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of the specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: rofecoxib, etoricoxib, parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$, integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J.*

Biol. Chem. 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another example of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an example, the neurokinin-1 receptor antagonist for use in conjunction with the compounds of the present invention is selected from: 2-(R)-(1-(R)-(3,5-bis(trifluoromethyl)phenypethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstarg); vinblastine (Velban®); vincristine (Oncovin®); vinorelbine (Navelbine®); vorinostat (Zolinza®) and zoledronate (Zometa®).

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCHinhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the structural Formula I may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of structural Formula I carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-di ethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of structural Formula I with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof.

Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with unsolvated and anhydrous forms.

Reference to the compounds of the invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

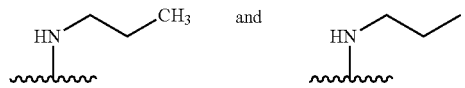

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of the invention which results in conversion in vivo to a compound within the scope of the invention is also within the scope of the invention. For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —COO— depending on the pH of the fluid or tissue where conversion takes place) or hydroxy form particularly in vivo and as such are encompassed within the scope of the invention. Examples of pharmaceutically acceptable pro-drug modifications include, but are not limited to, —$C_{1-6}$alkyl esters and —$C_{1-6}$alkyl substituted with phenyl esters.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Alkyl groups may be unsubstituted, or substituted with 1 to 3 substituents on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, haloaryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound. Unless otherwise specified, alkyl groups are unsubstituted.

Except where noted, the term "halogen" means fluorine, chlorine, bromine or iodine.

Except where noted, the term "saturated heterocycle" refers to a stable 4- to 7-membered mono-cyclic or stable 7- to 12-membered bicyclic or stable 12- to 14-membered tricyclic heteroatom-containing ring system unsubstituted or substituted with $C_{1-4}$ alkyl or halogen, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane and homopiperazine.

Except where noted herein, the term "unsaturated heterocycle" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Additional examples are pyridine, pyrimidine, thiophene, imidazole, isothiazole, oxadiazole, and isoxazole.

Except where noted herein, the term "unsaturated bicyclic heterocycle" or "unsaturated tricyclic heterocycle" refers to a heterocycle having fused rings in which at least one of the rings is not fully saturated, e.g.

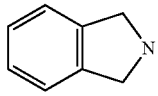

is a 9-membered unsaturated bicyclic heterocycle having one nitrogen atom.

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ monocyclic carbocycle, or a $C_9$ to $C_{12}$ bicyclic saturated or unsaturated ring, e.g., $C_{9-12}$ bicyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example

Unsaturated bicyclic carbocyclic ring systems include fused ring systems where all ring system members are carbon atoms and where at least one of the fused rings is not saturated.

Except where noted herein, the term "unsaturated bicyclic carbocycle" or "unsaturated tricyclic carbocycle" refers to a carbocycle having fused rings in which at least one of the rings is not fully saturated, e.g.

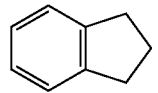

is a 9-membered unsaturated bicyclic carbocycle.

Except where noted, the term "aryl" refers to a stable 6- to 10-membered mono- or bicyclic unsaturated carbocyclic ring system such as phenyl, or naphthyl. The aryl ring can be unsubstituted or substituted with one or more of $C_{1-4}$ alkyl, hydroxyl, alkoxy, halogen, or amino.

"Celite®" (Fluka) diatomite is diatomaceous earth, and can be referred to as "celite".

Carbocycle groups may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $HS(O)_{0-2}$—, ($C_1$-$C_6$ alkyl)$S(O)_{0-2}$—, ($C_1$-$C_6$ alkyl)$S(O)_{0-2}$($C_1$-$C_6$ alkyl)-, $HS(O)_{0-2}$($C_1$-$C_6$ alkyl)-, ($C_1$-$C_6$ alkyl)$S(O)_{0-2}$, ($C_1$-$C_6$ alkyl)$C(O)NH$—, $HC(O)NH$—, $H_2N$—$C(NH)$—, —$O(C_1$-$C_6$ alkyl)$CF_3$, ($C_1$-$C_6$ alkyl)$C(O)$—, $HC(O)$—, ($C_1$-$C_6$ alkyl)$OC(O)$—, $HOC(O)$—, ($C_1$-$C_6$ alkyl)$O(C_1$-$C_6$ alkyl)-, $HO(C_1$-$C_6$ alkyl)-, ($C_1$-$C_6$ alkyl)$C(O)_{1-2}$($C_1$-$C_6$ alkyl)-, ($C_1$-$C_6$ alkyl)$C(O)_{1-2}$—, $HC(O)_{1-2}$($C_1$-$C_6$ alkyl)-, ($C_1$-$C_6$ alkyl)$OC(O)NH$—, $HOC(O)NH$—, —$P(O)(OH)_2$, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound. Unless otherwise specified, carbocycle groups are unsubstituted.

Heterocycles may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)$S(O)_{0-2}$—, $HS(O)_{0-2}$—, ($C_1$-$C_6$ alkyl)$S(O)_{0-2}$($C_1$-$C_6$ alkyl)-, $HS(O)_{0-2}$($C_1$-$C_6$ alkyl)-, ($C_1$-$C_6$ alkyl)$S(O)_{0-2}$—, ($C_1$-$C_6$ alkyl)$C(O)NH$—, $HC(O)NH$—, $H_2N$—$C(NH)$—, —$O(C_1$-$C_6$ alkyl)$CF_3$, $HC(O)$—, ($C_1$-$C_6$ alkyl)$C(O)$—, ($C_1$-$C_6$ alkyl)$OC(O)$—, $HOC(O)$—, ($C_1$-$C_6$ alkyl)$O(C_1$-$C_6$ alkyl)-, $HO(C_1$-$C_6$ alkyl)-, ($C_1$-$C_6$ alkyl)$O$—, (C alkyl)$C(O)_{1-2}$($C_1$-$C_6$ alkyl)-, $HC(O)_{1-2}$($C_1$-$C_6$ ($C_1$-$C_6$ alkyl)$C(O)_{1-2}$, ($C_1$-$C_6$ alkyl)$OC(O)NH$—, $HOC(O)NH$—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl. Heterocycles may also be independently substituted with a substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —$C(O)C_{1-6}$ alkyl, —$C(O)NHC_1$-$C_6$ alkyl, —$C(O)$ $NH_2$, —$C_1$-$C_6$ alkyl$C(O)$ $NH_2$, —$C_1$-$C_6$ alkyl$OC(O)NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound. Heterocycles may also be substituted as described above on one or more carbon atoms and one or more heteroatoms, where such substitutions result in formation of a stable compound. Unless otherwise specified, heterocycle groups are unsubstituted.

Except where noted herein, structures containing substituent variables such as variable "R" below:

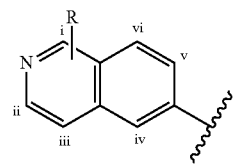

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, a bicyclic heterocycle can be a fused bicyclic heterocycle, e.g.,

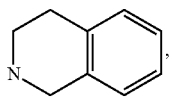

a bridged bicyclic heterocycle, e.g., or

or a spiro bicyclic heterocycle, e.g.,

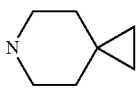

Where ring atoms are represented by variables such as "X", e.g,

the variables are defined by indicating the atom located at the variable ring position without depicting the ring bonds associated with the atom. For example, when X in the above ring is nitrogen, the definition will show "N" and will not depict the bonds associated with it, e.g., will not show "=N—". Likewise, when X is a carbon atom that is substituted with bromide, the definition will show "C—Br" and will not depict the bonds associated with it, e.g., will not show " 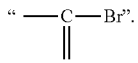 ".

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For the, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver about 0.01 mg per kg of body weight per day (mg/kg/day) to about 30 mg/kg/day, preferably 0.025-7.5 mg/kg/day, more preferably 0.1-2.5 mg/kg/day, and even more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula I hereinabove.

Methods for Making the Compounds of Present Invention
General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when a compound of structural Formula I has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

All solvents used were commercially available and were used without further purification. Reactions were typically run using anhydrous solvents under an inert atmosphere of nitrogen.

$^1$H spectra were recorded at 300 or 400 MHz for proton on a Bruker Mercury Plus 400 NMR Spectrometer equipped with a Bruker 400 BBO probe.

LCMS analyses were performed on a SHIMADZU LCMS consisting of an UFLC 20-AD and LCMS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.2 min with a total run time of 3.6 min. The column temperature was at 40° C. with the flow rate of 1.0 mL/min. The Diode Array Detector was scanned from 200-400 nm. The mass spectrometer was equipped with an electrospray ion source (ES) operated in a positive or negative mode.

HPLC analyses were performed on a SHIMADZU UFLC with two LC20 AD pump and a SPD-M20A Photodiiode Array Detector. The column used was an)(Bridge $C_{18}$, 3.5 μm, 4.6×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24} \cdot 4H_2O$, 5 g $(NH_4)_2Ce(IV)(NO_3)_6$ in 450 mL water and 50 mL concentrated $H_2SO_4$) to visualize the compound. Flash chromatography was preformed using 40-63 μm (230-400 mesh) silica gel from Silicycle following analogous techniques to those disclosed in Still, W. C.; Kahn, M.; and Mitra, M. Journal of Organic Chemistry, 1978, 43, 2923. Typical solvents used for flash chromatography or thin layer chromatography were mixtures of chloroform/methanol, dichloromethane/methanol, ethyl acetate/methanol and petroleum ether/ethyl acetate.

Preparative HPLC was performed on either a Waters Prep LC 4000 System using a Waters 2487 Diode Array or on a Waters LC Module 1 plus. The column used was SunFire Prep C18 OBD Column, 5 µm, 19×150 mm. Narrow gradients with acetonitrile/water, with the water containing either 0.1% trifluoroacetic acid or 0.1% $NH_4HCO_3$, were used to elute the compound at a flow rate of 20 mL/min and a total run time between 20-30 min. Detector, 254 nm, 220 nm.

Chiral HPLC conditions: Column, Chiralpak IA, 5 µm, 20×150 mm; Mobile phase, Hex/EtOH or IPA; Detector, 254 nm, 220 nm.

Starting materials used were either available from commercial sources or prepared according to literature procedures and had experimental data in accordance with those reported.

The following abbreviations have been used:

| ACN | acetonitrile |
|---|---|
| AcOH | acetic acid |
| Boc | tert-butoxycarbonyl |
| BSA | bovine serum albumin |
| BPO | benzoyl peroxide |
| ° C. | degree Celsius |
| $CCl_4$ | carbon tetrachloride |
| $CDCl_3$ | deuterated chloroform |
| $CD_3OD$ | deuterated methanol |
| CO | carbon monoxide |
| DCM | dichloromethane |
| DIEA | N,N-di si sopropylethylamine |
| DMAP | 4-(dimethylamino)pyridine |
| DMF | N,N-dimethylformamide |
| DMSO | dimethylsulfoxide |
| DTT | dithiothreitol |
| EDC | N-(3-dimethylaminpopropyl)-N'-ethylcarbodiimide |
| Et | ethyl |
| EtOAc | ethyl acetate |
| EtOH | ethanol |
| g | gram |
| h | hour(s) |
| HATU | N-[(Dimethylamino)-1H-1,2,3-triazolo-[4,5-b]pyridin-1-ylmethylene]-N-methylmethanaminium hexafluorophosphate N-oxide |
| HCl | hydrochloric acid |
| HPLC | high pressure liquid chromatography |
| iPrMgCl | isopropylmagnesium chlroide |
| LCMS | liquid chromatography and mass spectrometry |
| M | molar |
| Me | methyl |
| MeI | methyl iodide |
| MeOH | methanol |
| MS | mass spectrometry |
| MTBE | methyl tert-butyl ether |
| mmol | millimole |
| mg | milligram |
| min | minutes |
| mL | milliliter(s) |
| nM | nanomolar |
| N | normal |
| NaHMDS | sodium bis(trimethylsilyl)amide |
| $Na_2SO_4$ | sodium sulfate |
| NBS | N-bromosuccinimide |
| $NH_4HCO_3$ | ammonium bicarbonate |
| NMR | nuclear magnetic resonance |
| $PdCl_2$(dppf) | [1,1-bis(diphenylphosphine)ferrocene]dichloropalladium(II) |
| $Pd(PPh_3)_4$ | tetrakis(triphenylphosphine)palladium(0) |
| $POCl_3$ | phosphorus(V) oxychloride |
| psi | pound per square inch |
| RuPhos Pd $G_1$ | Chloro(2-dicyclohexylphosphino-2',6'-di-i-propoxy-1,1'-biphenyl)[2-(2-aminoethylphenyl)]palladium(II), methyl-t-butylether adduct |
| SFC | supercritical fluid chromatography |
| $SOCl_2$ | thionyl chloride |
| TEA | triethylamine |
| TFA | trifluoroacetic acid |
| THF | tetrahydrofuran |
| TLC | thin layer chromatography |
| TMS | tetramethylsilane |
| Prep-TLC | preparative TLC |
| µL | microliter |

General Synthetic Schemes

While the present invention has been described in conjunction with the specific examples set forth above, many alternatives, modifications and variations thereof will be apparent to those of ordinary skill in the art. All such alternatives, modifications and variations are intended to fall within the spirit and scope of the present invention.

Scheme 1

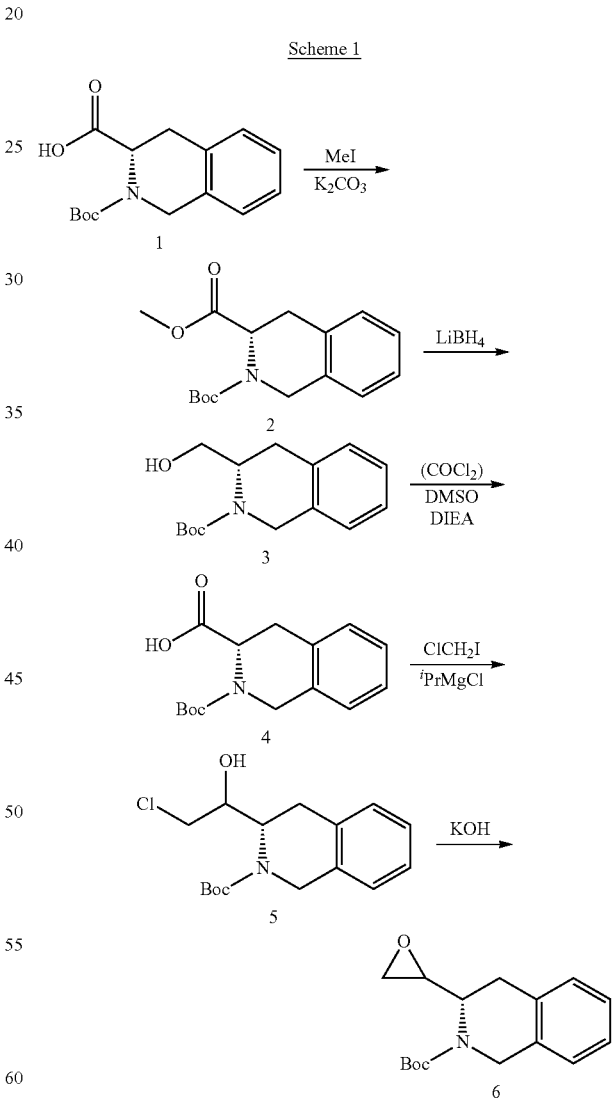

Compound 6 can be formed in the following sequence. Alkylation of acid 1 affords ester 2, while $LiBH_4$ reduction followed by Swern oxidation affords aldehyde 4. Alkyl magnesium chloride addition to aldehyde 4 affords alcohol 5, which cyclizes under basic conditions to give epoxide 6.

Scheme 2

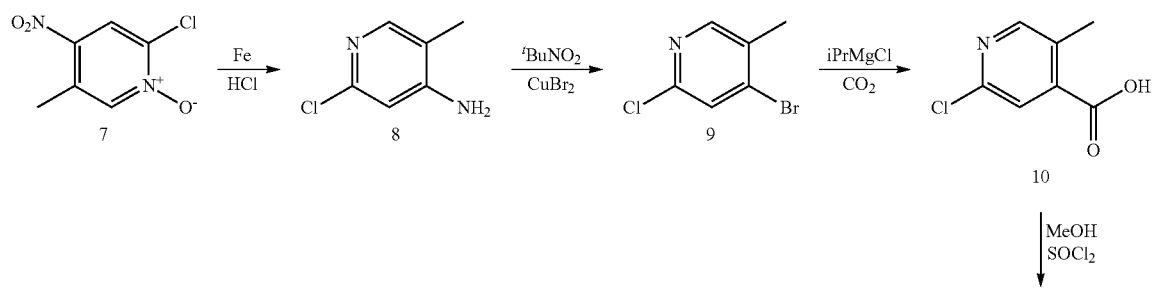

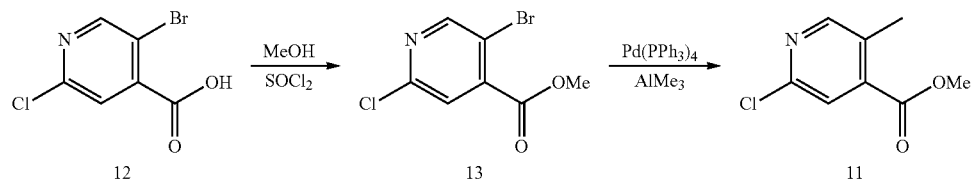

Compound 11 can be formed in the following sequence. Reduction of nitro 7 affords amino pyridine 8, which converts into pyridyl bromide 9 in the presence of tert-butyl nitroxide and copper bromide. Treating aryl bromide 9 with iPrMgCl and trapped by carbon dioxide affords acid 10, which undergoes esterification affords ester 11. Alternatively, compound 11 can be formed via a two-step sequence. Esterification of acid 12 affords ester 13 followed by Pd-catalyzed methylation of pyridyl bromide to afford compound 11.

Scheme 3

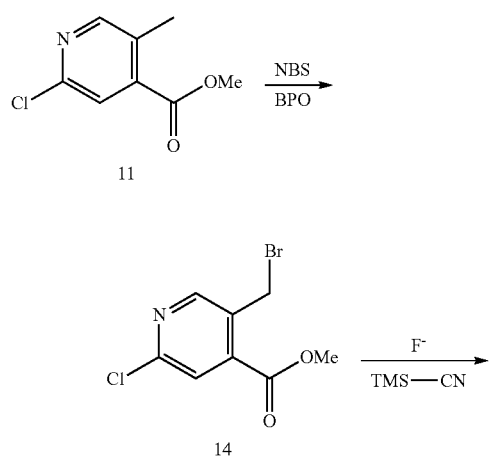

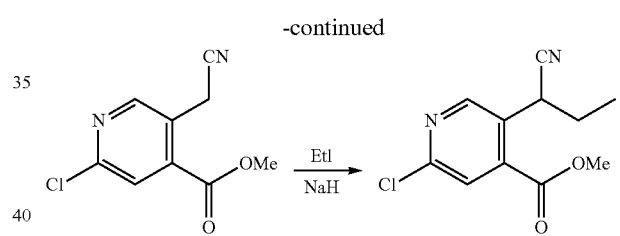

Compound 16 can be formed in the following sequence. Benzylic bromination of ester 11 affords bromide 16. Nucleophilic replacement of bromide 14 with TMSCN affords nitrile 15. Alkylation of 15 in the presence of NaH affords monoalkylated ester 16.

Scheme 4

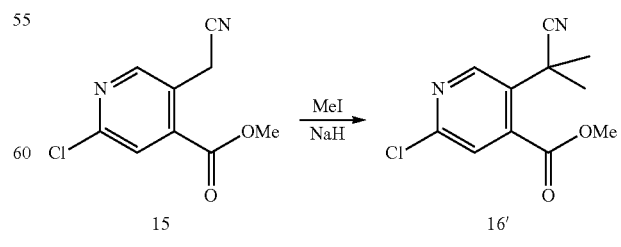

Compound 16 can be formed via double alkylation of compound 15 in the presence of NaH.

Scheme 5

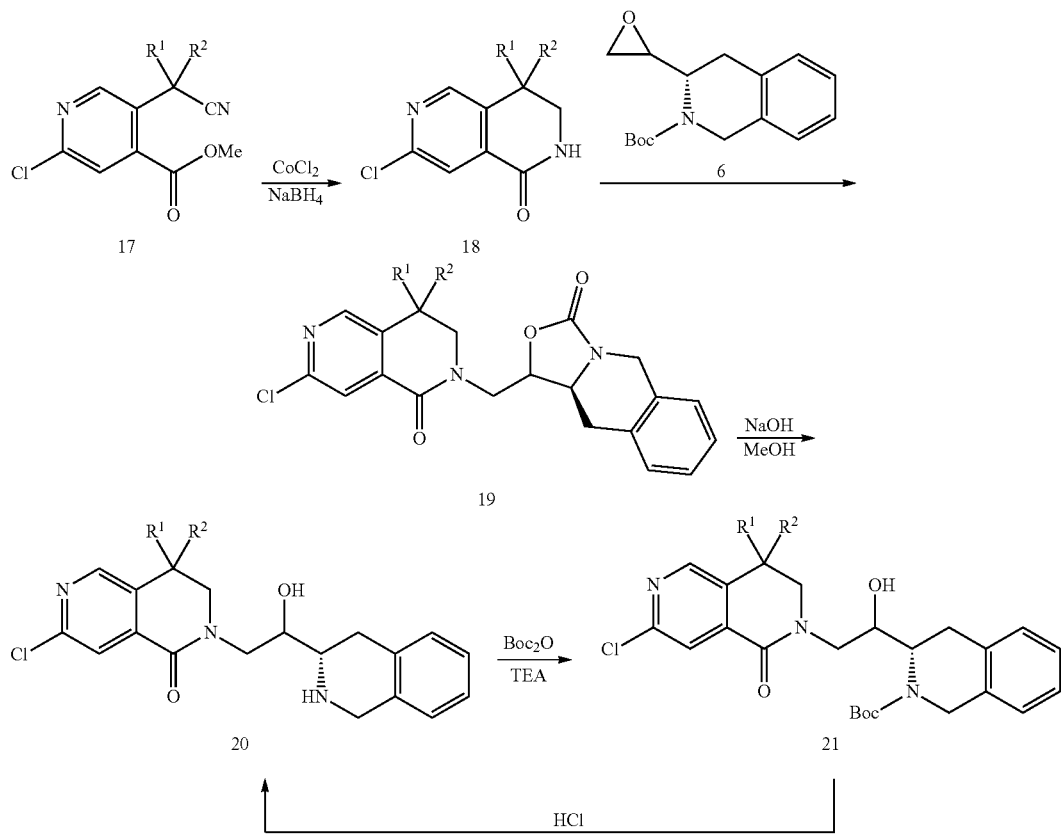

Compound of formula 20 can be formed in the following sequence. Reduction of nitrile 17 followed by ring closure affords lactam 18. Reacting lactam 18 with epoxide 6 affords intermediate 19, which upon deprotection under basic conditions affords compound of formula 20. Boc protection of compound 20 affords compound of formula 21, which can be converted back to compound 20 in the presence of acid.

Scheme 6

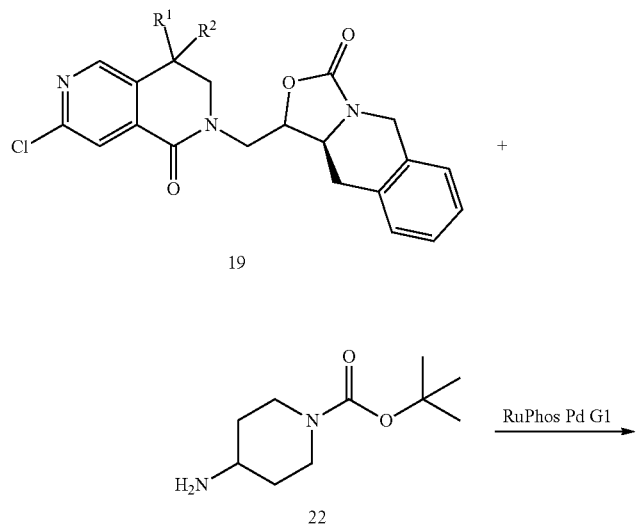

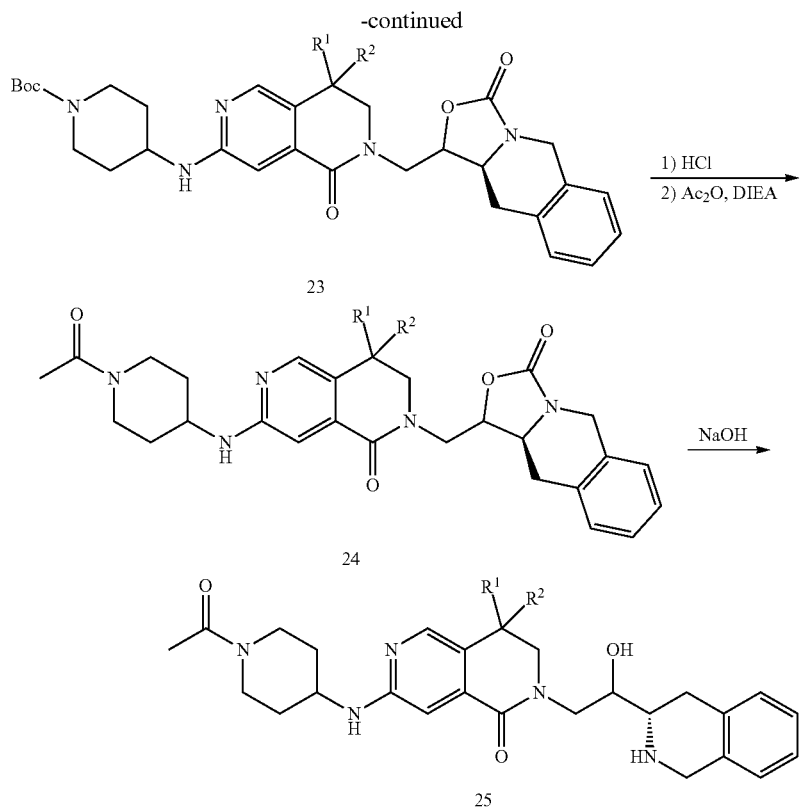

Compound of formula 25 can be formed in the following sequence. Pd-catalyzed C—N cross coupling between heterocyclic aryl chloride 19 and amine 22 affords amino pyridine 23. Boc deprotection under acidic conditions followed by acylation affords compound of formula 24. Deprotection under basic conditions affords compound 25.

INTERMEDIATES

Intermediate 1: tert-butyl (3S)-3-(oxiran-2-yl)-3,4-dihydroisoquinoline-2(1H)-carboxylate

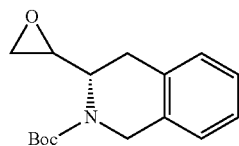 [SMILES: CC(C)(C)OC(=O)N1Cc2ccccc2C[C@H]1C1CO1]

Step 1: To a mixture of (S)-2-(tert-butoxycarbonyl)-1,2,3,4-tetrahydroisoquinoline-3-carboxylic acid (100 g, 361 mmol) and K$_2$CO$_3$ (150 g, 1082 mmol) in MeOH (500 ml) was added a solution of MeI (120 ml, 1916 mmol) in DMF (150 ml) at 30° C. The resulting solution was stirred at 30° C. for 72 h. Water (1500 mL) was then added and the mixture was extracted with EtOAc (500 mL×3). The separated organic layers were concentrated in vacuum and the resulting residue was purified by flash silica gel chromatography (eluting with ethyl acetate/pet. ether gradient) to give (S)-2-tert-butyl 3-methyl 3,4-dihydroisoquinoline-2,3(1H)-dicarboxylate as colorless oil. MS: 314 (M+23).

Step 2: To a solution of (S)-2-tert-butyl 3-methyl 3,4-dihydroisoquinoline-2,3(1H)-dicarboxylate (105 g, 360 mmol) in THF (600 ml) was added LiBH$_4$ (20.41 g, 937 mmol) slowly at 30° C. The mixture was stirred at 30° C. for 12 h. The mixture was diluted with water (1500 mL) and with ethyl acetate (200 mL). The resulting mixture was extracted with ethyl acetate (100 mL×3). The combined organic layers were washed with brine, dried over anhydrous Na$_2$SO$_4$, filtered and concentrated. The residue was purified by flash silica gel chromatography (eluting with ethyl acetate/pet. ether gradient) to give (S)-tert-butyl 3-(hydroxymethyl)-3,4-dihydroisoquinoline-2(1H)-carboxylate as colorless oil. MS: 286 (M+23).

Step 3: To a solution of oxalyl dichloride (32.4 ml, 383 mmol) in DCM (1300 mL) was added DMSO (54.3 ml, 766 mmol) in DCM (200 mL) at −78° C. The mixture was stirred at −78° C. for 30 min. To the mixture was then added (S)-tert-butyl 3-(hydroxymethyl)-3,4-dihydroisoquinoline-2(1H)-carboxylate (56 g, 213 mmol) in DCM (500 mL) at −78° C. The resulting mixture was stirred at −78° C. for 30 min. To the mixture was added TEA (213 ml, 1531 mmol) at −78° C. The resulting mixture was stirred at −78° C. for 30 min. The mixture was then diluted with water (1600 mL) and extracted with DCM (500 mL). The organic layer was adjusted to pH~5 with aq. HCl (0.1 M). The resulting mixture was washed with brine (1000 mL). The organic layer was dried over anhydrous Na$_2$SO$_4$, filtered, and concentrated to give the crude product (S)-tert-butyl 3-formyl-3,4-dihydroisoquinoline-2(1H)-carboxylate as yellow oil. This material was used without further purification in the next step.

Step 4: To a stirred solution of chloroiodomethane (46.6 g, 264 mmol) in THF (1500 ml) was added isopropylmagnesium chloride (106 ml, 211 mmol) at −78° C. under N$_2$ atmosphere. The solution was stirred at −78° C. for 20 min and then (S)-tert-butyl 3-formyl-3,4-dihydroisoquinoline-2

(1H)-carboxylate (46 g, 176 mmol) in THF (300 ml) was added. The resulting solution was stirred for 2 h at −78° C. The mixture was then diluted with saturated NH$_4$Cl (1000 mL) and EtOAc (500 mL). The mixture was extracted with EtOAc (500 mL×3). The combined organic layers were washed with brine (400 mL), dried over anhydrous Na$_2$SO$_4$, filtered, and concentrated. The residue was purified by flash silica gel chromatography (eluting with ethyl acetate/pet. ether gradient) to give (3S)-tert-butyl 3-(2-chloro-1-hydroxyethyl)-3,4-dihydroisoquinoline-2(1H)-carboxylate as yellow oil. MS: 334 (M+23).

Step 5: A stirred solution of (3S)-tert-butyl 3-(2-chloro-1-hydroxyethyl)-3,4-dihydroisoquinoline-2(1H)-carboxylate (15 g, 48.1 mmol) in THF (75 ml) was added KOH (13.17 g, 192 mmol) in MeOH (50 ml) dropwise at 0° C. The resulting solution was stirred at 20° C. for 0.5 h. The mixture was diluted with water (250 mL) and EtOAc (100 mL). The resulting mixture was extracted with EtOAc (100 mL×3). The combined organic layers were washed with brine (50 mL), dried over anhydrous Na$_2$SO$_4$, filtered, and concentrated to give tert-butyl (3S)-3-(oxiran-2-yl)-3,4-dihydroisoquinoline-2(1H)-carboxylate as brown oil which was used directly in the next step. MS: 298 (M+23).

Intermediate 2: tert-butyl (3S)-3-(2-(7-chloro-4-ethyl-1-oxo-3,4-dihydro-2,6-naphthyridin-2(1H)-yl)-1-hydroxyethyl)-3,4-dihydroisoquinoline-2(1H)-carboxylate

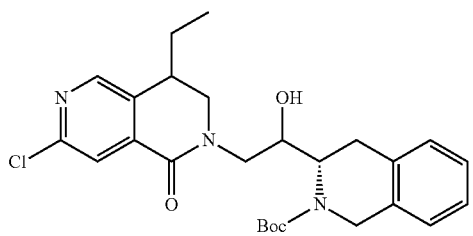 [SMILES: CCC1CN(CC(O)[C@@H]2Cc3ccccc3CN2C(=O)OC(C)(C)C)C(=O)c2cc(Cl)ncc21]

Step 1: To a mixture of 2-chloro-5-methyl-4-nitropyridine 1-oxide (50 g, 265 mmol) in acetic acid (200 mL) was added iron (74.0 g, 1326 mmol) at 30° C. The solution was stirred at 80° C. for 40 min. The mixture was poured into aq. NaOH (1M, 4000 mL) and extracted with EtOAc (1000 mL×3). The combined organic layers were washed with brine (800 mL), dried over anhydrous Na$_2$SO$_4$ and filtered. The filtrate was concentrated in vacuum to give 2-chloro-5-methylpyridin-4-amine as a light yellow oil, which was used directly without further purification. MS: 143 (M+1). $^1$H NMR (400 MHz, d4-methanol) δ 7.65 (s, 1H), 6.55 (s, 1H), 2.03 (s, 3H).

Step 2: To a mixture of tert-butyl nitrite (150 mL, 1262 mmol) in acetonitrile (1000 mL) was added copper(II) bromide (226 g, 1010 mmol) at 30° C. The solution was then stirred at 22° C. for 40 min and then cooled to 0° C. A solution of 2-chloro-5-methylpyridin-4-amine (120 g, 842 mmol) in acetonitrile (500 mL) was added at 0° C. The reaction was stirred at 0° C. for 1 h and then warmed to 22° C. and stirred for 12 h. The resulting mixture was concentrated in vacuum. The residue was dissolved in DCM (2000 mL), washed with aqueous NH$_3$ (15%, 2000 mL), dried over anhydrous Na$_2$SO$_4$, and filtered. The filtrate was concentrated in vacuum and the resulting residue was purified by flash silica gel chromatography (eluting with ethyl acetate/pet. ether gradient) to give 4-bromo-2-chloro-5-methylpyridine as colorless oil. MS: 206/208 (M+1/M+3). $^1$H NMR (400 MHz, CDCl$_3$) δ 8.14 (s, 1H), 7.48 (s, 1H), 2.30 (s, 3H).

Step 3: To a solution 4-bromo-2-chloro-5-methylpyridine (75 g, 363 mmol) in THF (500 mL) was added isopropylmagnesium chloride lithium chloride (1397 mL of 1.3M solution in THF, 1816 mmol) at 0° C., The resulting mixture stirred at 22° C. for 1 h. Then, the resulting mixture was stirred at 22° C. under CO$_2$ (1 atm) for 40 min. The mixture was quenched with H$_2$O (1500 mL) and extracted with EtOAc (300 mL×2). The aqueous phase was adjusted to pH~5 with 4 M aqueous HCl and then was extracted with EtOAc (300 mL×3). The resulting organic layers were washed with brine (300 mL) and concentrated in vacuum to give 2-chloro-5-methylisonicotinic acid as a light yellow solid, which was used directly in next step without further purification. MS: 172 (M+1). $^1$H NMR (400 MHz, DMSO-d$_6$) δ 8.39 (s, 1H), 7.68 (s, 1H), 2.43 (s, 3H).

Step 4: To a solution 2-chloro-5-methylisonicotinic acid (29 g, 169 mmol) in MeOH (200 mL) was added SOCl$_2$ (37.0 mL, 507 mmol) at 0° C. The resulting mixture was stirred at 80° C. for 12 h and then concentrated in vacuum. The residue was purified by flash silica gel chromatography (eluting with ethyl acetate/pet. ether gradient) to give methyl 2-chloro-5-methylisonicotinate as light yellow oil. MS: 186 (M+1). $^1$H NMR (400 MHz, CDCl$_3$) δ 8.32 (s, 1H), 7.73 (s, 1H), 3.93 (s, 3H), 2.52 (s, 3H).

Step 5: A mixture of methyl 2-chloro-5-methylisonicotinate (25 g, 135 mmol), NBS (21.58 g, 121 mmol) and BPO (4.89 g, 20.20 mmol) in CCl$_4$ (200 mL) was stirred at 80° C. for 3 h. The mixture was concentrated in vacuum and the residue was purified by flash silica gel chromatography (eluting with ethyl acetate/pet. ether gradient) to give methyl 5-(bromomethyl)-2-chloroisonicotinate as colorless oil. MS: 264/266 (M+1/M+3). $^1$H NMR (400 MHz, CDCl$_3$) δ 8.51 (s, 1H), 7.80 (s, 1H), 4.85 (s, 2H), 3.99 (s, 3H).

Step 6: A mixture of methyl 5-(bromomethyl)-2-chloroisonicotinate (26.5 g, 100 mmol), TMS-CN (67.2 mL, 501 mmol) and potassium fluoride (29.1 g, 501 mmol) in MeOH (200 mL) was stirred at 18° C. for 12 h. The reaction was concentrated in vacuum. The residue was purified by flash silica gel chromatography (eluting with ethyl acetate/pet. ether gradient) to give methyl 2-chloro-5-(cyanomethyl) isonicotinate as a yellow solid. MS: 211 (M+1). $^1$H NMR (400 MHz, CDCl$_3$) δ 8.61 (s, 1H), 7.92 (s, 1H), 4.14 (s, 2H), 3.99 (s, 3H).

Step 7: To a mixture of methyl 2-chloro-5-(cyanomethyl) isonicotinate (15.7 g, 74.5 mmol) in DMF (100 mL) was slowly added NaH (3.28 g, 82 mmol) at 15° C. The mixture was stirred at 15° C. for 0.5 h. Iodoethane (6.59 mL, 82 mmol) was then added to the mixture at 15° C. The resulting mixture was stirred at 15° C. for 2 h. The reaction was quenched with water (500 mL) and extracted with EtOAc (100 mL×3). The combined organic layers were washed with brine (150 mL), dried over anhydrous Na$_2$SO$_4$, filtered, and concentrated. The residue was purified by flash silica gel chromatography (eluting with ethyl acetate/pet. ether gradient) to give methyl 2-chloro-5-(1-cyanopropyl)isonicotinate as colorless oil. $^1$H NMR (400 MHz, CDCl$_3$) δ 8.72 (s, 1H), 7.84 (s, 1H), 4.85-4.89 (m, 1H), 3.97 (s, 3H), 1.87-1.97 (m, 2H), 1.15 (t, J=4.8, 3H).

Step 8: To a mixture of methyl 2-chloro-5-(1-cyanopropyl) isonicotinate (14 g, 58.7 mmol) in MeOH (150 mL) was added cobalt(II) chloride (45.7 g, 352 mmol) at 0° C. and followed by addition of NaBH$_4$ (13.32 g, 352 mmol). The mixture was stirred at 0° C. for 0.5 h and then quenched with sat. aqueous NH$_4$Cl (500 mL). The aqueous layer was extracted with EtOAc (80 mL×3). The combined organic layers were dried over anhydrous Na₂SO₄, filtered, and concentrated in vacuum. The residue was purified by flash silica gel chromatography (eluting with ethyl acetate/pet. ether gradient) to afford 7-chloro-4-ethyl-3,4-dihydro-2,6-naphthyridin-1(2H)-one as a white solid. MS: 2H (M+1).

Step 9: To a solution of NaH (0.068 g, 1.709 mmol) in DMF (6 mL) was added 7-chloro-4-ethyl-3,4-dihydro-2,6-naphthyridin-1(2H)-one (0.3 g, 1.424 mmol). The mixture was stirred at 15° C. for 0.5 h. Then, to the mixture was added tert-butyl (3S)-3-(oxiran-2-yl)-3,4-dihydroisoquinoline-2 (1H)-carboxylate (0.471 g, 1.709 mmol). The reaction was stirred at 20° C. for 16 h. The mixture was then quenched with water (50 mL) and extracted with EtOAc (20 mL×3). The organic layers were concentrated in vacuum and the resulting residue was purified by reverse phase HPLC (ACN/water with 0.1% TFA modifier) to give (10aS)-1-((7-chloro-4-ethyl-1-oxo-3,4-dihydro-2,6-naphthyridin-2(1H)-yl)methyl)-10,10a-dihydro-/H-oxazolo[3,4-b]isoquinolin-3(5H)-one as a mixture of 4 stereoisomers as a white solid. MS: 412 (M+1). ¹H NMR (400 MHz, CDCl₃) δ 8.38 (s, 1H), 7.90 (s, 1H), 7.13-7.25 (m, 4H), 4.62-4.98 (m, 2H), 4.32-4.43 (m, 1H), 3.98-4.26 (m, 2H), 3.66-3.82 (m, 3H), 3.11-3.26 (m, 1H), 2.67-2.91 (m, 2H), 1.70-1.80 (m, 2H), 0.97-1.05 (m, 3H).

Step 10: To a solution of (10aS)-1-((7-chloro-4-ethyl-1-oxo-3,4-dihydro-2,6-naphthyridin-2(1H)-yl)methyl)-10,10a-dihydro-/H-oxazolo[3,4-b]isoquinolin-3(5H)-one (600 mg, 1.457 mmol) in MeOH (5 mL) and water (5 mL) was added NaOH (233 mg, 5.83 mmol) at 20° C. The resulting solution was stirred at 70° C. for 12 h. Water (40 mL) was added, and the mixture was extracted with EtOAc (20 mL×3). The organic layers were concentrated in vacuum to give 7-chloro-4-ethyl-2-(2-hydroxy-2-((S)-1,2,3,4-tetrahydroisoquinolin-3-yl)ethyl)-3,4-dihydro-2,6-naphthyridin-1(2H)-one as a mixture of 4 stereoisomers as a light yellow solid which was used directly in next step without further purification. MS: 386 (M+1).

Step 11: To a solution of 7-chloro-4-ethyl-2-(2-hydroxy-2-((S)-1,2,3,4-tetrahydroisoquinolin-3-yl)ethyl)-3,4-dihydro-2,6-naphthyridin-1(2H)-one (1.4 g, 3.63 mmol) in DCM (15 mL) was added di-tert-butyl dicarbonate (1.264 mL, 5.44 mmol) and DIEA (1.267 mL, 7.26 mmol). The reaction was stirred at 15° C. for 1 h. The mixture was concentrated in vacuum and purified by flash silica gel chromatography (eluting with ethyl acetate/pet. ether gradient) to give tert-butyl (3S)-3-(2-(7-chloro-4-ethyl-1-oxo-3,4-dihydro-2,6-naphthyridin-2(1H)-yl)-1-hydroxyethyl)-3,4-dihydroisoquinoline-2(1H)-carboxylate as a mixture of 4 stereoisomers as a yellow solid. MS: 486 (M+1).

EXAMPLES 1-4

Example 1: 7-chloro-4-ethyl-2-(2-hydroxy-2-((S)-1,2,3,4-tetrahydroisoquinolin-3-yl)ethyl)-3,4-dihydro-2,6-naphthyridin-1(2H)-one Isomer 1

Example 2: 7-chloro-4-ethyl-2-(2-hydroxy-2-((S)-1,2,3,4-tetrahydroisoquinolin-3-yl)ethyl)-3,4-dihydro-2,6-naphthyridin-1(2H)-one Isomer 2

Example 3: 7-chloro-4-ethyl-2-(2-hydroxy-2-((S)-1,2,3,4-tetrahydroisoquinolin-3-yl)ethyl)-3,4-dihydro-2,6-naphthyridin-1(2H)-one Isomer 3

Example 4; 7-chloro-4-ethyl-2-(2-hydroxy-2-((S)-1,2,3,4-tetrahydroisoquinolin-3-yl)ethyl)-3,4-dihydro-2,6-naphthyridin-1(2H)-one Isomer 4

Each of the following structures corresponds to one of the above-referenced isomers:

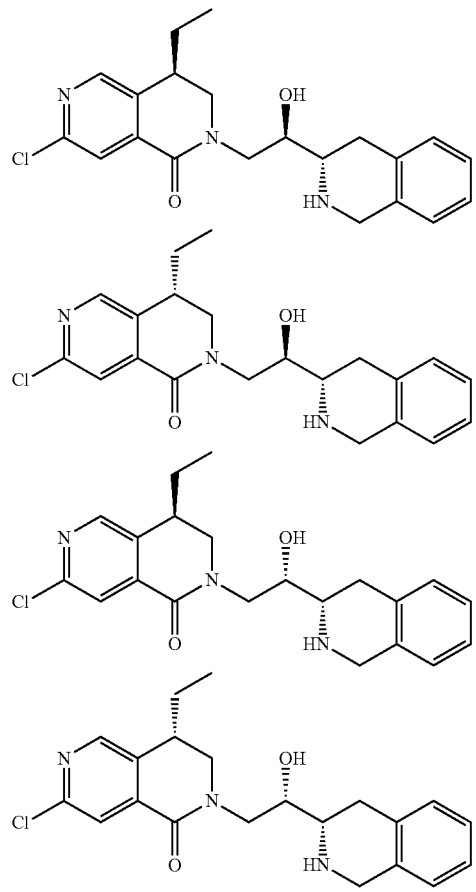

Step 1: The four stereoisomers of tert-butyl (3S)-3-(2-(7-chloro-4-ethyl-1-oxo-3,4-dihydro-2,6-naphthyridin-2(1H)-yl)-1-hydroxyethyl)-3,4-dihydroisoquinoline-2(1H)-carboxylate were separated by chiral SFC (AS column, 15%/60% ethanol/CO₂) to afford:

Isomer 1 (first eluting): ¹H NMR (400 MHz, CD₃OD) δ 8.26 (s, 1H), 7.65 (s, 1H), 7.07 (s, 4H), 4.24-4.34 (m, 2H), 3.68-4.04 (m, 4H), 3.46 (d, J=3.6, 1H), 3.08-3.12 (m, 2H), 2.81-2.84 (m, 2H), 1.57 (t, J=7.6 Hz, 2H), 1.42 (s, 9H), 0.85 (t, J=7.2 Hz, 3H);

Isomer 2 (second eluting): ¹H NMR (400 MHz, CD₃OD) δ 8.24 (s, 1H), 7.66 (s, 1H), 7.06 (s, 4H), 4.79-4.83 (m, 1H), 4.24-4.45 (m, 2H), 3.65-3.93 (m, 4H), 2.80-3.12 (m, 4H), 1.59-1.64 (m, 2H), 1.42 (s, 9H), 0.85 (t, J=7.2 Hz, 3H);

Isomer 3 (third eluting): ¹H NMR (400 MHz, CD₃OD) δ 8.26 (s, 1H), 7.69 (s, 1H), 7.03-7.08 (m, 4H), 4.70 (m, 1H), 4.19-4.26 (m, 2H), 3.69-3.76 (m, 4H), 3.56-3.59 (m, 1H), 2.80-2.95 (m, 3H), 1.42-1.58 (m, 2H), 1.33-1.40 (m, 9H), 0.85 (t, J=7.6 Hz, 3H);

Isomer 4 (fourth eluting): ¹H NMR (400 MHz, CD₃OD) δ 8.27 (s, 1H), 7.68 (s, 1H), 7.03-7.08 (m, 4H), 4.69-4.74 (m, 1H), 4.17-4.28 (m, 2H), 3.70-3.81 (m, 3H), 3.34-3.58 (m, 2H), 2.93-2.96 (m, 2H), 2.79 (s, 1H), 1.56-1.65 (m, 2H), 1.38 (m, 9H), 0.85 (t, J=7.6 Hz, 3H).

Step 2: A solution of tert-butyl (3S)-3-(2-(7-chloro-4-ethyl-1-oxo-3,4-dihydro-2,6-naphthyridin-2(1H)-yl)-1-hydroxyethyl)-3,4-dihydroisoquinoline-2(1H)-carboxylate Isomer 1 (30 mg, 0.062 mmol) in HCl (10 mL of 4 M solution in EtOAc) was stirred at 15° C. for 10 min. The reaction was concentrated in vacuum and the resulting residue was purified by reverse phase HPLC (ACN/water with 0.1% ammonium bicarbonate modifier) to give 7-chloro-4-ethyl-2-(2-hydroxy-2-((S)-1,2,3,4-tetrahydroisoquinolin-3-yl)ethyl)-3,4-dihydro-2,6-naphthyridin-1(2H)-one Isomer 1 (Example 1) as a white solid. MS: 386 (M+1). $^1$H NMR (400 MHz, CD$_3$OD) δ 8.42 (s, 1H), 7.85 (s, 1H), 7.05-7.15 (m, 4H), 3.95-4.05 (m, 5H), 3.65-3.76 (m, 2H), 2.91-2.96 (m, 4H), 1.69-1.81 (m, 2H), 1.03 (t, J=7.6 Hz, 3H).

The other isomers were prepared using the methodology herein and the general procedure described above.

Example 2 (derived from tert-butyl (3S)-3-(2-(7-chloro-4-ethyl-1-oxo-3,4-dihydro-2,6-naphthyridin-2(1H)-yl)-1-hydroxyethyl)-3,4-dihydroisoquinoline-2(1H)-carboxylate Isomer 2): MS: 386 (M+1). $^1$H NMR (400 MHz, CD$_3$OD) δ 8.41 (s, 1H), 7.85 (s, 1H), 7.06-7.16 (m, 4H), 3.90-4.06 (m, 5H), 3.69-3.80 (m, 2H), 2.92-2.99 (m, 4H), 1.70-1.83 (m, 2H), 1.04 (t, J=8.0 Hz, 3H).

Example 3 (derived from tert-butyl (3S)-3-(2-(7-chloro-4-ethyl-1-oxo-3,4-dihydro-2,6-naphthyridin-2(1H)-yl)-1-hydroxyethyl)-3,4-dihydroisoquinoline-2(1H)-carboxylate Isomer 3): MS: 386 (M+1). $^1$H NMR (400 MHz, CD$_3$OD) δ 8.42 (s, 1H), 7.85 (s, 1H), 7.07-7.15 (m, 4H), 3.88-4.06 (m, 5H), 3.66-3.81 (m, 2H), 2.86-2.89 (m, 4H), 1.71-1.85 (m, 2H), 1.04 (t, J=7.6 Hz, 3H).

Example 4 (derived from tert-butyl (3S)-3-(2-(7-chloro-4-ethyl-1-oxo-3,4-dihydro-2,6-naphthyridin-2(1H)-yl)-1-hydroxyethyl)-3,4-dihydroisoquinoline-2(1H)-carboxylate Isomer 4): MS: 386 (M+1). $^1$H NMR (400 MHz, CD$_3$OD) δ 8.41 (s, 1H), 7.85 (s, 1H), 7.07-7.15 (m, 4H), 3.99-4.06 (m, 4H), 3.57-3.74 (m, 3H), 2.86-2.91 (m, 4H), 1.71-1.78 (m, 2H), 1.03 (t, J=7.2 Hz, 3H).

EXAMPLES 5 and 6

Example 5: 7-((1-acetylpiperidin-4-yl)amino)-2-(2-hydroxy-2-((S)-1,2,3,4-tetrahydroisoquinolin-3-yl)ethyl)-3,4-dihydro-2,6-naphthyridin-1(2H)-one Isomer 1 and Example 6: 7-((1-acetylpiperidin-4-yl)amino)-2-(2-hydroxy-2-((S)-1,2,3,4-tetrahydroisoquinolin-3-yl)ethyl)-3,4-dihydro-2,6-naphthyridin-1(2H)-one Isomer 2

Each of the following structures corresponds to one of the above-referenced isomers:

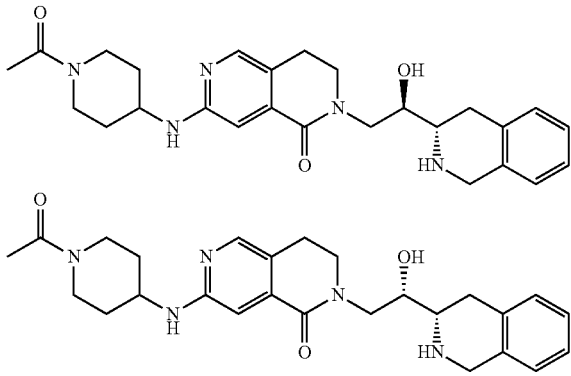

Step 1: To a solution of 5-bromo-2-chloroisonicotinic acid (30 g, 127 mmol) in MeOH (300 mL) was added SOCl$_2$ (27.8 mL, 381 mmol) at 0° C. The solution was then heated to and stirred at 80° C. for 10 h. The resulting mixture was concentrated in vacuum and the residue was purified by flash silica gel chromatography (eluting with ethyl acetate/pet. ether gradient) to give methyl 5-bromo-2-chloroisonicotinate as colorless oil. MS: 250/252 (M+1/M+3). $^1$H NMR (400 MHz, CDCl$_3$) δ 8.58 (s, 1H), 7.63 (s, 1H), 3.94 (s, 3H).

Step 2: To a mixture of methyl 5-bromo-2-chloroisonicotinate (10 g, 39.9 mmol) and Pd(Ph$_3$P)$_4$ (4.61 g, 3.99 mmol) in THF (100 mL) was added trimethylaluminum (26.0 mL, 51.9 mmol) at 25° C. The mixture was then heated to and stirred at 80° C. for 6 h. Water (5 mL) was added to quench the reaction and the mixture was concentrated in vacuum. The residue was purified by flash silica gel chromatography (eluting with ethyl acetate/pet. ether gradient) to give methyl 2-chloro-5-methylisonicotinate as a colorless oil. MS: 186 (M+1). $^1$H NMR (400 MHz, CDCl$_3$) δ 8.29 (s, 1H), 7.70 (s, 1H), 3.91 (s, 3H), 2.49 (s, 3H).

Step 3: A mixture of methyl 2-chloro-5-methylisonicotinate (12 g, 64.7 mmol), NBS (10.36 g, 58.2 mmol) and BPO (2.35 g, 9.70 mmol) in CCl$_4$ (100 mL) was stirred at 80° C. for 12 h. The mixture was concentrated in vacuum and the residue was purified by flash silica gel chromatography (eluting with ethyl acetate/pet. ether gradient) to give methyl 5-(bromomethyl)-2-chloroisonicotinate as colorless oil. MS: 264/266 (M+1/M+3). $^1$H NMR (400 MHz, CDCl$_3$) δ 8.50 (s, 1H), 7.80 (s, 1H), 4.85 (s, 2H), 3.99 (s, 3H).

Step 4: To a mixture of methyl 5-(bromomethyl)-2-chloroisonicotinate (10 g, 37.8 mmol) and cesium fluoride (28.7 g, 189 mmol) in MeOH (80 mL) was added TMS-CN (25.3 mL, 189 mmol) at 30° C. The solution was stirred at 30° C. for 12 h. The reaction was filtered and the filtrate was concentrated in vacuum. The resulting residue was purified by flash silica gel chromatography (eluting with ethyl acetate/pet. ether gradient) to afford methyl 2-chloro-5-(cyanomethyl)isonicotinate as a white solid. MS: 211 (M+1). $^1$H NMR (400 MHz, CDCl$_3$) δ 8.60 (s, 1H), 7.91 (s, 1H), 4.14 (s, 2H), 3.99 (s, 3H).

Step 5: To a mixture of methyl 2-chloro-5-(cyanomethyl)isonicotinate (1.6 g, 7.60 mmol) in MeOH (20 mL) was added cobalt(II) chloride (5.92 g, 45.6 mmol) at 0° C. NaBH$_4$ (1.72 g, 45.6 mmol) was then added. The mixture was stirred at 0° C. for 0.5 h. The solution was then quenched with saturated aqueous ammonium chloride (50 mL). The aqueous layer was extracted with EtOAc (20 mL×3). The combined organic extracts were dried over anhydrous sodium sulfate, filtered, and concentrated in vacuum to afford 7-chloro-3,4-dihydro-2,6-naphthyridin-1(2H)-one as a yellow solid, which was used directly in the next step without further purification. MS: 183 (M+1).

Step 6: To a solution of 7-chloro-3,4-dihydro-2,6-naphthyridin-1(2H)-one (450 mg, 2.464 mmol) in DMF (8 mL) was added NaH (148 mg, 3.7 mmol) and the reaction mixture was stirred at 80° C. for 0.5 h. To the mixture was then added tert-butyl (3S)-3-(oxiran-2-yl)-3,4-dihydroisoquinoline-2(1H)-carboxylate (814 mg, 2.96 mmol). The reaction was stirred at 80° C. for 16 h. The reaction mixture was cooled to room temperature and then directly purified by prep-HPLC (ACN/water with 0.1% TFA modifier) to give (10aS)-1-((7-chloro-1-oxo-3,4-dihydro-2,6-naphthyridin-2(1H)-yl)methyl)-10,10a-dihydro-/H-oxazolo[3,4-b]isoquinolin-3(5H)-one, TFA salt as a yellow solid. MS: 384 (M+1).

Step 7: To a solution of (10aS)-1-((7-chloro-1-oxo-3,4-dihydro-2,6-naphthyridin-2(1H)-yl)methyl)-10,10a-dihydro-/H-oxazolo[3,4-b]isoquinolin-3(5H)-one (220 mg, 0.573 mmol) and tert-butyl 4-aminopiperidine-1-carboxylate (172 mg, 0.86 mmol) in THF (5 mL) was added Cs$_2$CO$_3$ (467 mg, 1.43 mmol) and RuPhos Pd G$_1$ (94 mg, 0.115 mmol) in a glove-box. The reaction was stirred at 80° C. for 16 h. The mixture was quenched with water (20 mL) and extracted with EtOAc (15 mL×3). The combined organic layers were washed with brine (20 mL), dried over anhydrous sodium sulfate, filtered, and concentrated. The resulting residue was purified by prep-TLC (Pet. ether:EtOAc=1:3) to give tert-butyl 4-((5-oxo-6-(((10aS)-3-oxo-3,5,10,10a-tetrahydro-1H-oxazolo[3,4-b]isoquinolin-1-yl)methyl)-5,6,7,8-tetrahydro-2,6-naphthyridin-3-yl)amino)piperidine-1-carboxylate as a brown solid. MS: 570 (M+23).

Step 8: A solution of tert-butyl 4-((5-oxo-6-(((10aS)-3-oxo-3,5,10,10a-tetrahydro-1H-oxazolo[3,4-b]isoquinolin-1-yl)methyl)-5,6,7,8-tetrahydro-2,6-naphthyridin-3-yl)amino)piperidine-1-carboxylate (210 mg, 0.383 mmol) in HCl (3 mL of a 4 M solution in EtOAc) was stirred at 26° C. for 1.5 h. The mixture was then concentrated under reduced pressure to give (10aS)-1-((1-oxo-7-(piperidin-4-ylamino)-3,4-dihydro-2,6-naphthyridin-2(1H)-yl)methyl)-10,10a-dihydro-/H-oxazolo[3,4-b]isoquinolin-3(5H)-one as a brown solid, which was used directly in the next step without further purification. MS: 448 (M+1).

Step 9: To a solution of (10aS)-1-(1-oxo-7-(piperidin-4-ylamino)-3,4-dihydro-2,6-naphthyridin-2(1H)-yl)methyl)-10,10a-dihydro-/H-oxazolo[3,4-b]isoquinolin-3(5H)-one (218 mg, 0.49 mmol) in DCM (5 mL) was added acetic anhydride (59.7 mg, 0.59 mmol) and DIEA (0.17 mL, 0.97 mmol). The reaction was stirred at 26° C. for 2 h. Water (20 mL) was then added and the resulting mixture was extracted with DCM (15 mL×3). The combined organic layers were washed with brine (20 mL), dried over anhydrous sodium sulfate, filtered, and concentrated to give (10aS)-1-(7-((1-acetylpiperidin-4-yl)amino)-1-oxo-3,4-dihydro-2,6-naphthyridin-2(1H)-yl)methyl)-10,10a-dihydro-/H-oxazolo[3,4-b]isoquinolin-3(5H)-one as a brown solid. MS: 490 (M+1). The crude product was used directly in the next step without further purification.

Step 10: (10aS)-1-((7-((1-acetylpiperidin-4-yl)amino)-1-oxo-3,4-dihydro-2,6-naphthyridin-2(1H)-yl)methyl)-10,10a-dihydro-/H-oxazolo[3,4-b]isoquinolin-3(5H)-one (200 mg, 0.41 mmol) was separated by SFC (OD column, 55%/55% EtOH/CO$_2$) to afford (10aS)-1-((7-((1-acetylpiperidin-4-yl)amino)-1-oxo-3,4-dihydro-2,6-naphthyridin-2(1H)-yl)methyl)-10,10a-dihydro-/H-oxazolo[3,4-b]isoquinolin-3(5H)-one Isomer 1 (first eluting) as a white solid and (10aS)-1-((7-((1-acetylpiperidin-4-yl)amino)-1-oxo-3,4-dihydro-2,6-naphthyridin-2(1H)-yl)methyl)-10,10a-dihydro-/H-oxazolo[3,4-b]isoquinolin-3(5H)-one Isomer 2 (second eluting) as a white solid. MS: 490 (M+1).

Step 11: To a mixture of (10aS)-1-((7-((1-acetylpiperidin-4-yl)amino)-1-oxo-3,4-dihydro-2,6-naphthyridin-2(1H)-yl)methyl)-10,10a-dihydro-/H-oxazolo[3,4-b]isoquinolin-3(5H)-one Isomer 1 (31 mg, 0.063 mmol) in THF (2 mL) and water (2 mL) was added NaOH (5.1 mg, 0.13 mmol) at 20° C. The solution was then stirred at 70° C. for 8 h. The mixture was concentrated and purified by HPLC (ACN/water with 0.1% TFA modifier) to give 7-((1-acetylpiperidin-4-yl)amino)-2-(2-hydroxy-2-((S)-1,2,3,4-tetrahydroisoquinolin-3-yl)ethyl)-3,4-dihydro-2,6-naphthyridin-1(2H)-one, TFA salt Isomer 1 as a yellow solid. This material was taken up in ACN and washed with aqueous ammonia to give 7-((1-acetylpiperidin-4-yl)amino)-2-(2-hydroxy-2-((S)-1,2,3,4-tetrahydroisoquinolin-3-yl)ethyl)-3,4-dihydro-2,6-naphthyridin-1(2H)-one Isomer 1 (Example 5) as a white solid as free base. MS: 464 (M+1). $^1$H NMR (400 MHz, CD$_3$OD) δ 7.94 (s, 1H), 7.09-7.18 (m, 3H), 7.04-7.09 (m, 1H), 7.03 (s, 1H), 4.40-4.43 (m, 1H), 3.87-4.14 (m, 6H), 3.69-3.84 (m, 2H), 3.58-3.63 (m, 1H), 3.25-3.32 (m, 1H), 2.82-3.00 (m, 6H), 2.13 (s, 3H), 1.97-2.12 (m, 2H), 1.29-1.54 (m, 2H).

Example 6: 7-((1-acetylpiperidin-4-yl)amino)-2-(2-hydroxy-2-((S)-1,2,3,4-tetrahydroisoquinolin-3-yl)ethyl)-3,4-dihydro-2,6-naphthyridin-1(2H)-one Isomer 2 was prepared following an analogous procedure as described for Example 5 but starting with (10aS)-1-((7-((1-acetylpiperidin-4-yl)amino)-1-oxo-3,4-dihydro-2,6-naphthyridin-2(1H)-yl)methyl)-10,10a-dihydro-/H-oxazolo[3,4-b]isoquinolin-3(5H)-one Isomer 2

Example 6: MS: 464 (M+1). $^1$H NMR (400 MHz, CD$_3$OD) δ 7.92 (s, 1H), 7.09-7.15 (m, 3H), 7.06 (br d, J=4.82 Hz, 1H), 7.01 (s, 1H), 4.37-4.40 (m, 1H), 3.99-4.11 (m, 2H), 3.82-3.99 (m, 4H), 3.66-3.81 (m, 2H), 3.50-3.56 (m, 1H), 3.23-3.29 (m, 1H), 2.76-2.98 (m, 6H), 2.11 (s, 3H), 1.94-2.10 (m, 2H), 1.25-1.52 (m, 2H).

EXAMPLES 7-10

Example 7: 7-((1-acetylpiperidin-4-yl)amino)-4-ethyl-2-(2-hydroxy-2-((S)-1,2,3,4-tetrahydroisoquinolin-3-yl)ethyl)-3,4-dihydro-2,6-naphthyridin-1(2H)-one Isomer 1

Example 8: 7-((1-acetylpiperidin-4-yl)amino)-4-ethyl-2-(2-hydroxy-2-((S)-1,2,3,4-tetrahydroisoquinolin-3-yl)ethyl)-3,4-dihydro-2,6-naphthyridin-1(2H)-one Isomer 2

Example 9: 7-((1-acetylpiperidin-4-yl)amino)-4-ethyl-2-(2-hydroxy-2-((S)-1,2,3,4-tetrahydroisoquinolin-3-yl)ethyl)-3,4-dihydro-2,6-naphthyridin-1(2H)-one Isomer 3-1

Example 10: 7-((1-acetylpiperidin-4-yl)amino)-4-ethyl-2-(2-hydroxy-2-((S)-1,2,3,4-tetrahydroisoquinolin-3-yl)ethyl)-3,4-dihydro-2,6-naphthyridin-1(2H)-one Isomer 3-2

Each of the following structures corresponds to one of the above-referenced isomers:

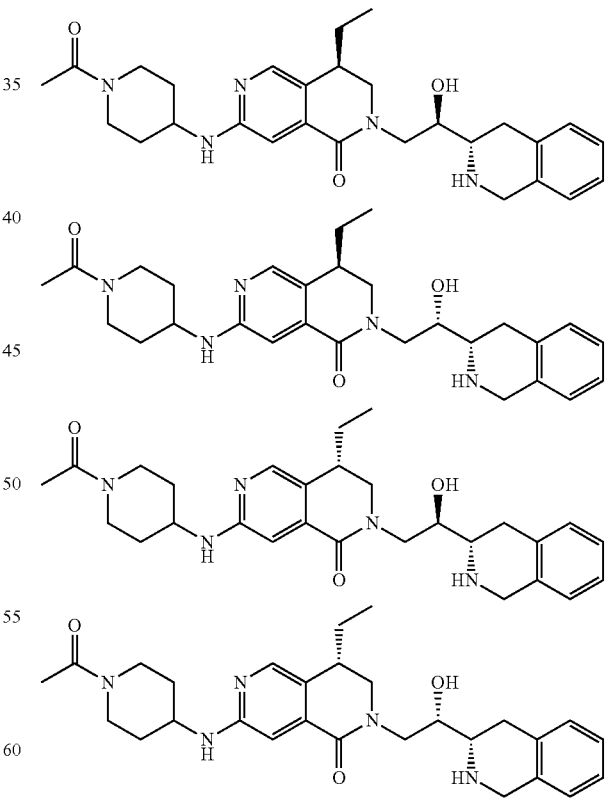

Step 1: To a solution of (10aS)-1-((7-chloro-4-ethyl-1-oxo-3,4-dihydro-2,6-naphthyridin-2(1H)-yl)methyl)-10,10a-dihydro-/H-oxazolo[3,4-b]isoquinolin-3(5H)-one (120 mg, 0.291 mmol) and tert-butyl 4-aminopiperidine-1-carboxylate (88 mg, 0.437 mmol) in THF (2 mL) was added Cs$_2$CO$_3$ (237 mg, 0.73 mmol) and RuPhos Pd G1 (47.6 mg, 0.058 mmol) in glove-box. The reaction was stirred at 80° C. for 16 h. The mixture was cooled and directly purified by prep-TLC(Pet. ether:EtOAc=1:2) to give tert-butyl 4-((8-ethyl-5-oxo-6-(((10aS)-3-oxo-3,5,10,10a-tetrahydro-/H-oxazolo[3,4-b]isoquinolin-1-yl)methyl)-5,6,7,8-tetrahydro-2,6-naphthyridin-3-yl)amino)piperidine-1-carboxylate as a brown solid. MS: 576 (M+1).

Step 2: A solution of tert-butyl 4-((8-ethyl-5-oxo-6-(((10aS)-3-oxo-3,5,10,10a-tetrahydro-/H-oxazolo[3,4-b]isoquinolin-1-yl)methyl)-5,6,7,8-tetrahydro-2,6-naphthyridin-3-yl)amino)piperidine-1-carboxylate (260 mg, 0.452 mmol) in HCl (10 mL of a 4 M solution in EtOAc) was stirred at 13° C. for 1 h. The mixture was then concentrated under reduced pressure to give (10aS)-1-((4-ethyl-1-oxo-7-(piperidin-4-ylamino)-3,4-dihydro-2,6-naphthyridin-2(1H)-yl)methyl)-10,10a-dihydro-/H-oxazolo[3,4-b]isoquinolin-3(5H)-one as a brown solid, which was used directly in the next step without further purification.

Step 3: To a solution of (10aS)-1-((4-ethyl-1-oxo-7-(piperidin-4-ylamino)-3,4-dihydro-2,6-naphthyridin-2(1H)-yl)methyl)-10,10a-dihydro-/H-oxazolo[3,4-b]isoquinolin-3 (5H)-one (210 mg, 0.44 mmol) in DCM (5 mL) was added acetic anhydride (54 mg, 0.530 mmol) and DIEA (0.154 mL, 0.88 mmol). The reaction was stirred at 15° C. for 1 h. The mixture was purified by prep-TLC (DCM:MeOH=10:1) to give (10aS)-1-((7-((1-acetylpiperidin-4-yl)amino)-4-ethyl-1-oxo-3,4-dihydro-2,6-naphthyridin-2(1H)-yl)methyl)-10,10a-dihydro-/H-oxazolo[3,4-b]isoquinolin-3(5H)-one as a white solid. MS: 518 (M+1).

Step 4: To a mixture of (10aS)-1-((7-((1-acetylpiperidin-4-yl)amino)-4-ethyl-1-oxo-3,4-dihydro-2,6-naphthyridin-2(1H)-yl)methyl)-10,10a-dihydro-/H-oxazolo[3,4-b]isoquinolin-3(5H)-one (180 mg, 0.348 mmol) in MeOH (2 mL) and water (2 mL) was added NaOH (27.8 mg, 0.695 mmol) at 20° C., then the solution was stirred at 70° C. for 12 h. The mixture was concentrated and purified by reverse phase HPLC (ACN/water with 0.1% TFA modifier) to give 4-ethyl-2-(2-hydroxy-2-((S)-1,2,3,4-tetrahydroisoquinolin-3-yl)ethyl)-7-(piperidin-4-ylamino)-3,4-dihydro-2,6-naphthyridin-1(2H)-one as a light yellow solid. MS: 450 (M+1). $^1$H NMR (400 MHz, CD$_3$OD) δ 7.93 (s, 1H), 7.37 (s, 1H), 7.24-7.29 (m, 4H), 4.40 (s, 2H), 3.95-4.10 (m, 4H), 3.47-3.69 (m, 4H), 3.12-3.26 (m, 5H), 2.88 (s, 1H), 2.26 (m, 2H), 1.68-1.81 (m, 4H), 1.01 (t, J=4.0 Hz, 3H).

Step 5: To a solution of 4-ethyl-2-(2-hydroxy-2-((S)-1,2,3,4-tetrahydroisoquinolin-3-yl)ethyl)-7-(piperidin-4-ylamino)-3,4-dihydro-2,6-naphthyridin-1(2H)-one (140 mg, 0.311 mmol) in DCM (5 ml) was added 2,5-dioxocyclopentyl acetate (48.6 mg, 0.311 mmol) and DIEA (0.109 mL, 0.623 mmol). The reaction was stirred at 15° C. for 10 min. The mixture was concentrated in vacuum and the resulting residue was purified by reverse phase HPLC (ACN/water with 0.1% TFA modifier) to give 7-((1-acetylpiperidin-4-yl)amino)-4-ethyl-2-(2-hydroxy-2-((S)-1,2,3,4-tetrahydroisoquinolin-3-yl)ethyl)-3,4-dihydro-2,6-naphthyridin-1(2H)-one as a white solid. MS: 492 (M+1).

The stereoisomers were separated by chiral SFC (AD column, 55%/55% IPA/CO$_2$) to afford four isomers:

Example 7 (first eluting): $^1$H NMR (400 MHz, CD$_3$OD) δ 7.92 (s, 1H), 7.00-7.13 (m, 5H), 4.38-4.63 (m, 1H), 3.90-4.05 (m, 7H), 3.53-3.64 (m, 2H), 3.25 (s, 1H), 2.88-2.91 (m, 4H), 2.75 (s, 1H), 2.11 (s, 3H), 1.99-2.07 (m, 2H), 1.64-1.67 (m, 2H), 1.43-1.62 (m, 2H), 0.94 (t, J=7.2 Hz, 3H)

Example 8 (second eluting): $^1$H NMR (400 MHz, CD$_3$OD) δ 7.92 (s, 1H), 7.00-7.12 (m, 5H), 4.39 (m, 1H), 3.82-4.04 (m, 7H), 3.64-3.67 (m, 2H), 3.19-3.28 (m, 1H), 2.74-2.89 (m, 5H), 2.06-2.11 (m, 5H), 1.62-1.69 (m, 2H), 1.28-1.58 (m, 2H), 0.98 (t, J=7.6 Hz, 3H)

The third eluting was further separated by chiral SFC (AD column, 55%/55% ethanol/CO$_2$) to afford another two isomers:

Example 9 (first eluting of the second round SFC): $^1$H NMR (400 MHz, CD$_3$OD) δ 7.92 (s, 1H), 7.01-7.13 (m, 5H), 4.40 (m, 1H), 3.83-4.05 (m, 7H), 3.64-3.67 (m, 2H), 3.21-3.25 (m, 1H), 2.74-2.92 (m, 5H), 1.99-2.11 (m, 5H), 1.64-1.70 (m, 2H), 1.39-1.62 (m, 2H), 0.98 (t, J=7.6 Hz, 3H)

Example 10 (second eluting of the second round SFC): $^1$H NMR (400 MHz, CD$_3$OD) δ 7.92 (s, 1H), 7.01-7.14 (m, 5H), 4.40 (m, 1H), 3.89-4.08 (m, 7H), 3.59-3.63 (m, 2H), 3.18-3.21 (m, 1H), 2.75-2.93 (m, 5H), 1.99-2.13 (m, 5H), 1.63-1.67 (m, 2H), 1.36-1.47 (m, 2H), 0.98 (t, J=7.6 Hz, 3H).

EXAMPLES 11 and 12

Example 11: 7-((1-acetylpiperidin-4-yl)amino)-2-(2-hydroxy-2-((S)-1,2,3,4-tetrahydroisoquinolin-3-yl)ethyl)-4,4-dimethyl-3,4-dihydro-2,6-naphthyridin-1(2H)-one Isomer 1

Example 12: 7-((1-acetylpiperidin-4-yl)amino)-2-(2-hydroxy-2-((S)-1,2,3,4-tetrahydroisoquinolin-3-yl)ethyl)-4,4-dimethyl-3,4-dihydro-2,6-naphthyridin-1(2H)-one Isomer 2

Each of the following structures corresponds to one of the above-referenced isomers:

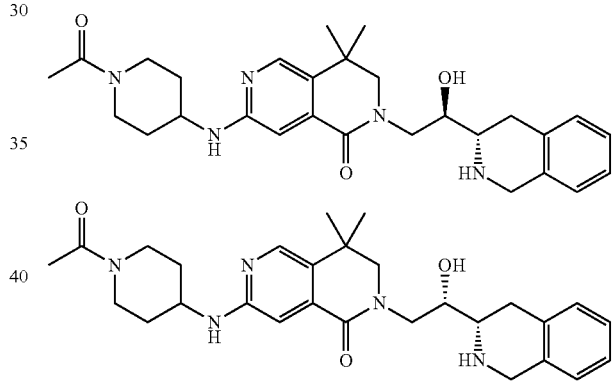

Step 1: To a mixture of methyl 2-chloro-5-(cyanomethyl) isonicotinate (2.6 g, 12.34 mmol) in DMF (20 mL) was slowly added NaH (1.481 g, 37.0 mmol) at 8° C. The mixture was stirred at 8° C. for 0.5 h. Iodomethane (8.76 g, 61.7 mmol) was then added at 8° C. and the mixture was stirred at 8° C. for 2 h. Water (100 mL) was then added and the resulting mixture was extracted with EtOAc (50 mL×3). The combined organic layers were washed with brine (100 mL), dried over anhydrous sodium sulfate, and concentrated. The residue was purified by flash silica gel chromatography (eluting with ethyl acetate/pet. ether gradient) to give methyl 2-chloro-5-(2-cyanopropan-2-yl)isonicotinate as a white solid. MS: 239 (M+1). $^1$H NMR (400 MHz, CDCl$_3$) δ 8.53 (s, 1H), 7.49 (s, 1H), 3.99 (s, 3H), 1.89 (s, 6H).

Step 2: To a mixture of methyl 2-chloro-5-(2-cyanopropan-2-yl)isonicotinate (1.4 g, 5.87 mmol) in MeOH (20 mL) was added cobalt(II) chloride (4.57 g, 35.2 mmol) at 0° C. Then, NaBH$_4$ (1.332 g, 35.2 mmol) was added. The mixture was stirred at 0° C. for 0.5 h. The solution was quenched with saturated aqueous NH$_4$Cl (50 mL). The aqueous layer was extracted with EtOAc (20 mL×3). The combined organic extracts were dried over anhydrous sodium sulfate, filtered, and concentrated in vacuum. The residue was purified by flash silica gel chromatography (eluting with ethyl acetate/pet. ether gradient) to afford 7-chloro-4,4-dimethyl-3,4-dihydro-2,6-naphthyridin-1(2H)-one as a white solid. MS: 211 (M+1). $^1$H NMR (400 MHz, CDCl$_3$) δ 8.44 (s, 1H), 7.86-7.93 (m, 1H), 3.36 (d, J=3.07 Hz, 2H), 1.37-1.49 (m, 6H).

Step 3: To a solution of NaH (22.78 mg, 0.570 mmol) in DMF (2 mL) was added 7-chloro-4,4-dimethyl-3,4-dihydro-2,6-naphthyridin-1(2H)-one (100 mg, 0.475 mmol) and the reaction was stirred at 15° C. for 30 minutes. Then, to the mixture was added tert-butyl (3S)-3-(oxiran-2-yl)-3,4-dihydroisoquinoline-2(1H)-carboxylate (196 mg, 0.712 mmol). The reaction was stirred at 20° C. for 16 h. Water (20 mL) was added and then the mixture was extracted with EtOAc (15 mL×3). The combined organic layers were washed with brine (20 mL), dried over anhydrous sodium sulfate, and concentrated. The residue was purified by reverse phase HPLC (acetonitrile/water with 0.1% TFA modifier) to give (10aS)-1-((7-chloro-4,4-dimethyl-1-oxo-3,4-dihydro-2,6-naphthyridin-2(1H)-yl)methyl)-10,10a-dihydro-/H-oxazolo[3,4-b]isoquinolin-3(5H)-one, TFA salt as a white solid. MS: 412 (M+1).

Step 4: To a solution of (10aS)-1-((7-chloro-4,4-dimethyl-1-oxo-3,4-dihydro-2,6-naphthyridin-2(1H)-yl)methyl)-10,10a-dihydro-/H-oxazolo[3,4-b]isoquinolin-3(5H)-one (50 mg, 0.121 mmol) and tert-butyl 4-aminopiperidine-1-carboxylate (36.5 mg, 0.182 mmol) in THF (5 mL) was added Cs$_2$CO$_3$ (99 mg, 0.303 mmol) and RuPhos Pd G$_1$ (19.83 mg, 0.024 mmol) in glove-box. The reaction was stirred at 80° C. for 16 h. Water (20 mL) was added and the resulting mixture was extracted with EtOAc (15 mL×3). The combined organic layers were washed with brine (20 mL), dried over anhydrous sodium sulfate, filtered, and concentrated. The residue was purified by prep-TLC (Pet. ether:EtOAc=1:3) to give tert-butyl 4-((8,8-dimethyl-5-oxo-6-(((10aS)-3-oxo-3,5,10,10a-tetrahydro-/H-oxazolo[3,4-b]isoquinolin-1-yl)methyl)-5,6,7,8-tetrahydro-2,6-naphthyridin-3-yl)amino)piperidine-1-carboxylate as a brown solid. MS: 576 (M+1).

Step 5: A solution of tert-butyl 4-((8,8-dimethyl-5-oxo-6-(((10aS)-3-oxo-3,5,10,10a-tetrahydro-1H-oxazolo[3,4-b]isoquinolin-1-yl)methyl)-5,6,7,8-tetrahydro-2,6-naphthyridin-3-yl)amino)piperidine-1-carboxylate (110 mg, 0.191 mmol) in HCl (3 mL of a 4 M solution in EtOAc) was stirred at 10° C. for 1 h. The mixture was concentrated to give (10aS)-1-((4,4-dimethyl-1-oxo-7-(piperidin-4-ylamino)-3,4-dihydro-2,6-naphthyridin-2(1H)-yl)methyl)-10,10a-dihydro-1H-oxazolo[3,4-b]isoquinolin-3(5H)-one as a white solid, which was used in the next step without further purification. MS: 476 (M+1).

Step 6: To a solution of (10aS)-1-((4,4-dimethyl-1-oxo-7-(piperidin-4-ylamino)-3,4-dihydro-2,6-naphthyridin-2(1H)-yl)methyl)-10,10a-dihydro-/H-oxazolo[3,4-b]isoquinolin-3(5H)-one (100 mg, 0.210 mmol) in DCM (5 mL) was added acetic anhydride (25.8 mg, 0.252 mmol) and DIEA (0.073 mL, 0.421 mmol). The reaction was stirred at 10° C. for 1 h. The mixture was concentrated to give (10aS)-1-((7-((1-acetylpiperidin-4-yl)amino)-4,4-dimethyl-1-oxo-3,4-dihydro-2,6-naphthyridin-2(1H)-yl)methyl)-10,10a-dihydro-/H-oxazolo[3,4-b]isoquinolin-3(5H)-one as a brown solid. MS: 518 (M+1).

Step 7: (10aS)-1-((7-((1-acetylpiperidin-4-yl)amino)-4,4-dimethyl-1-oxo-3,4-dihydro-2,6-naphthyridin-2(1H)-yl)methyl)-10,10a-dihydro-/H-oxazolo[3,4-b]isoquinolin-3(5H)-one (100 mg, 0.193 mmol) was purified by chiral SFC (OD column, 45%/45% EtOH/CO$_2$) to afford two isomers as white solids: Isomer 1 (first eluting) and Isomer 2 (second eluting).

Step 8: To a mixture of (10aS)-1-((7-((1-acetylpiperidin-4-yl)amino)-4,4-dimethyl-1-oxo-3,4-dihydro-2,6-naphthyridin-2(1H)-yl)methyl)-10,10a-dihydro-/H-oxazolo[3,4-b]isoquinolin-3(5H)-one Isomer 1 (40 mg, 0.077 mmol) in MeOH (0.5 mL) and water (0.5 mL) was added NaOH (6.18 mg, 0.155 mmol) at 10° C. The solution was then heated to and stirred at 65° C. for 16 h. The mixture was concentrated and purified by prep-HPLC (ACN/water with 0.1% ammonium hydroxide modifier) to give 7-((1-acetylpiperidin-4-yl)amino)-2-(2-hydroxy-2-((S)-1,2,3,4-tetrahydroisoquinolin-3-yl)ethyl)-4,4-dimethyl-3,4-dihydro-2,6-naphthyridin-1(2H)-one Isomer 1 (Example 11) as a white solid. MS: 492 (M+1). $^1$H NMR (400 MHz, CD$_3$OD) δ 8.00 (s, 1H), 7.09-7.15 (m, 3H), 7.06 (br d, J=4.82 Hz, 1H), 7.01 (s, 1H), 4.38-4.41 (m, 1H), 3.98-4.11 (m, 2H), 3.81-3.98 (m, 4H), 3.53-3.66 (m, 2H), 3.43-3.52 (m, 1H), 3.21-3.29 (m, 1H), 2.76-2.96 (m, 4H), 2.11 (s, 3H), 1.95-2.10 (m, 2H), 1.38-1.51 (m, 2H), 1.35 (br s, 3H), 1.34 (br s, 3H).

Example 12: 7-((1-acetylpiperidin-4-yl)amino)-2-(2-hydroxy-2-((S)-1,2,3,4-tetrahydroisoquinolin-3-yl)ethyl)-4,4-dimethyl-3,4-dihydro-2,6-naphthyridin-1(2H)-one Isomer 2 was prepared in an anlogous fashion starting with (10aS)-1-((7-((1-acetylpiperidin-4-yl)amino)-4,4-dimethyl-1-oxo-3,4-dihydro-2,6-naphthyridin-2(1H)-yl)methyl)-10,10a-dihydro-1H-oxazolo[3,4-b]isoquinolin-3(5H)-one Isomer 2: MS: 492 (M+1). $^1$H NMR (400 MHz, CD$_3$OD) δ 8.00 (s, 1H), 7.12 (s, 3H), 7.05 (br s, 1H), 7.00 (s, 1H), 4.38-4.41 (m, 1H), 3.85-4.10 (m, 6H), 3.52-3.66 (m, 2H), 3.44-3.52 (m, 1H), 3.25 (br s, 1H), 2.83-2.98 (m, 4H), 2.11 (s, 3H), 1.94-2.09 (m, 2H), 1.43-1.47 (br m, 2H), 1.35 (s, 6H).

PRMT5-MEP50 Enzyme Methylation Assay

PRMT5/MEP50 biochemical assay is a direct measurement of the methylation activity of the enzyme complex on a short peptide substrate derived from the N-terminus of H4 histone. Methylation experiment is performed with recombinant protein. The assessment of inhibitory effect (IC$_{50}$) of small molecules is measured by the effectiveness of the compounds to inhibit this reaction.

In this assay, the potency (IC$_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 0.5 nM of Full-length (FL)-PRMT5-MEP50 enzyme complex (recombinant proteins from baculovirus-transfected Sf21 cells: FL-PRMT5; MW=73837 kDa and FL-MEP50; MW=38614). Plates were sealed and placed in a 37° C. humidified chamber for 30 minutes pre-incubation with compounds. Subsequently, each reaction was initiated by the addition of 2 μL 1× assay buffer containing 75 nM biotinylated H4R3(Me1) peptide, and 15 μM S-(5'-Adenosyl)-L-Methionine Chloride (SAM). The final reaction in each well of 10 μL consists of 0.5 nM PRMT5-MEP50, 75 nM biotinylated-peptide, and 15 μM. Methylation reactions were allowed to proceed for 150 minutes in a sealed plate at 37° C. Reactions were immediately quenched by the addition of 1 μL of 10% formic acid. Plates were then frozen and shipped to SAMDI™ Tech Inc. to determine the percent conversion from K4R3(Me1) to K4R3(Me2). IC$_{50}$ values were determined by 7 parameters biphasic fit model plotting the percent product conversion vs. ($Log_{10}$) compound concentrations.

PRMT5 Cell Target Engagement (TE) Assay

The PRMT5 TE assay is a biomarker assay for identifying compounds that inhibit symmetric dimethylation of arginine (SDMA) of PRMT5 substrates. This assay detects symmetrically dimethylated nuclear proteins using high content imaging technology. Detection of the expression of symmetrically dimethylated nucleo proteins is through a mixture of primary rabbit monoclonal antibodies to SDMA (CST 13222), which in turn recognized by an Alexafluor 488 dye-conjugated anti-rabbit IgG secondary antibody. The IN Cell Analyzer 2200 measures nuclear Alexafluor 488 fluorescent dye intensity that is directly related to the level of expression of symmetrically dimethylated nuclear proteins at the single cell level. Nuclear AF488 dye intensities are compared to the mean value for DMSO treated cells (MIN) to report percent of inhibition for each compound-treated well.

In this assay, the cell potency ($EC_{50}$) of each compound was determined from a ten point (1:3 serial dilution; top compound concentration of 10000 nM) titration curve using the following outlined procedure. Each well of a BD falcon collagen coated black/clear bottom 384-well plate was seeded with 4000 MCF-7 cells and allowed to attach for 5 hours. Media from cell plate was removed at 0.5 mm above the bottom of the plate and replaced with 30 µL of fresh media containing 1.2× compounds in 0.1% DMSO. Cells were treated for 3 days in 37° C. $CO_2$ incubator. On day 3, cells were fixed with Cytofix, permeablized with 0.4% Triton-X-100/Cytofix, and washed with D-PBS without Ca/Mg. Cells were blocked with Licor Odessey blocking reagent for one hour at room temperature, followed by incubation with anti-SDMA (1:1000) antibody at 4° C. overnight. 1° antibody was removed, followed by three washings with DPBS without Ca/Mg and 0.05% Tween20. Hoechst (5 µg/ml), Cell Mask deep stain (1:2000) and Alexa488-conjugated goat anti-rabbit IgG (2 µg/mL) was added for 1 hour at room temperature. A final washing step (three washes) was performed before sealing plate for imaging on In Cell Analyzer 2200. Images from analyzer were uploaded to Columbus (at WP) for image analysis. $IC_{50}$ values were determined by 4 parameters robust fit of percent fluorescence units vs. ($Log_{10}$) compound concentrations.

| Ex. No. | Enzyme Methylation Assay ($IC_{50}\_1$, nM; $IC_{50}\_2$, nM) | TE Assay ($EC_{50}$, nM) |
| --- | --- | --- |
| 1 | 5187; 100000 | 10000 |
| 2 | 3835; 100000 | 10000 |
| 3 | 28250; 100000 | 10000 |
| 4 | 42920; 100000 | 10000 |
| 5 | 10.84; 8160 | 1590 |
| 6 | 481.5; 100000 | 10000 |
| 7 | 7.15; 4987 | 682.3 |
| 8 | 96.8; 29100 | 3245 |
| 9 | 1.08; 1184 | 102.9 |
| 10 | 272; 64520 | 10000 |
| 11 | 56.89; 9226 | 3895 |
| 12 | 1.53; 631 | 102.4 |

What is claimed is:

1. A compound of formula I,

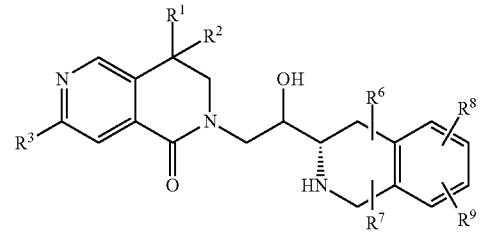

or a pharmaceutically acceptable salt thereof, wherein
$R^1$ is hydrogen or $C_{1-4}$ alkyl, and
$R^2$ is hydrogen or $C_{1-4}$ alkyl, or
$R^1$ and $R^2$, together with the atom to which they are attached, form a $C_{3-6}$ cycloalkyl ring;
$R^3$ is halogen or —$NHR^4$;
$R^4$ is a 5- or 6-membered saturated heterocycle, unsubstituted or substituted with one, two, or three moieties independently selected from the group consisting of $C(O)R^5$ and halogen;
$R^5$ is $C_{1-4}$ alkyl; and
$R^6$, $R^7$, $R^8$, and $R^9$, are independently selected from hydrogen, halogen and $C_{1-4}$ alkyl.

2. A compound of claim 1, or a pharmaceutically acceptable salt thereof, wherein
$R^1$ is hydrogen or $C_{1-4}$ alkyl, and
$R^2$ is hydrogen or $C_{1-4}$ alkyl, or
$R^1$ and $R^2$, together with the atom to which they are attached, form a $C_{3-6}$ cycloalkyl ring;
$R^3$ is halogen or —$NHR^4$;
$R^4$ is a 5- or 6-membered saturated heterocycle containing 1 N atom, wherein the heterocycle is unsubstituted or substituted with one, two, or three moieties independently selected from the group consisting of $C(O)R^5$ and halogen;
$R^5$ is $C_{1-4}$ alkyl; and
$R^6$, $R^7$, $R^8$, and $R^9$ are independently selected from hydrogen, halogen and $C_{1-4}$ alkyl.

3. A compound of claim 2, or a pharmaceutically acceptable salt thereof, wherein
$R^1$ is hydrogen or $C_{1-4}$ alkyl;
$R^2$ is hydrogen or $C_{1-4}$ alkyl;
$R^3$ is halogen or —$NHR^4$;
$R^4$ is a 6-membered saturated heterocycle containing 1 N atom, wherein the heterocycle is unsubstituted or substituted with $C(O)R^5$; and
$R^5$ is $C_{1-4}$ alkyl.

4. A compound of claim 3, or a pharmaceutically acceptable salt thereof, where $R^1$ is hydrogen, $CH_3$ or $CH_2CH_3$.

5. A compound of claim 3, or a pharmaceutically acceptable salt thereof, where $R^2$ is hydrogen or $CH_3$.

6. A compound of claim 3, or a pharmaceutically acceptable salt thereof, where $R^3$ is
Cl, or

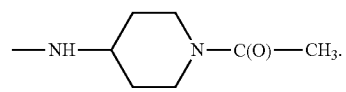

7. A compound of claim 2, which is
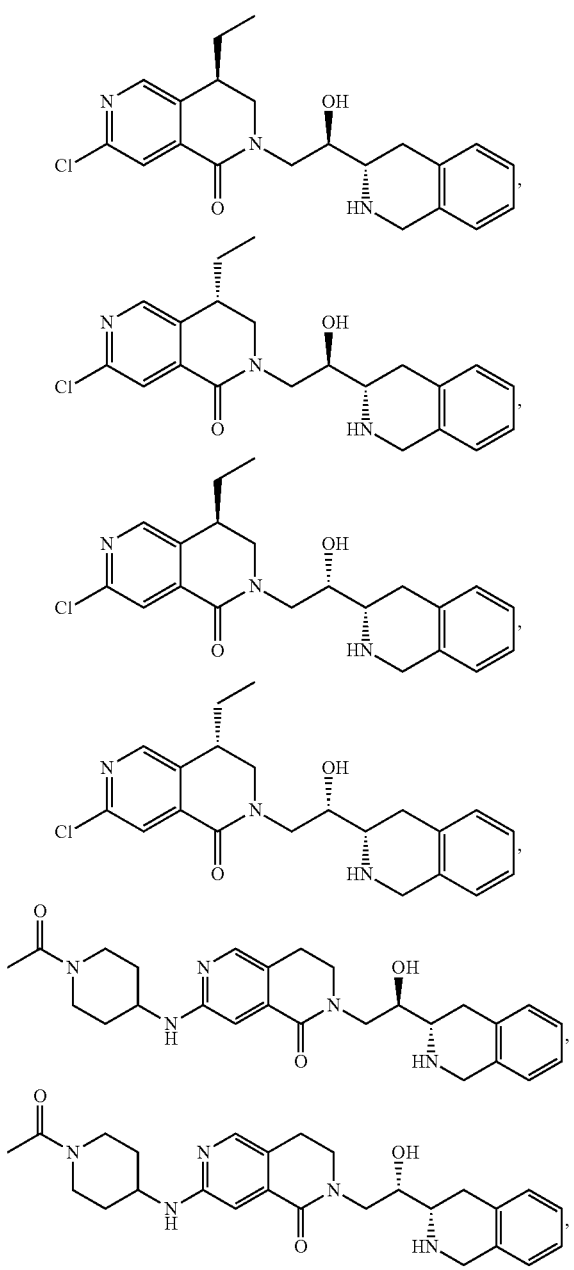
-continued
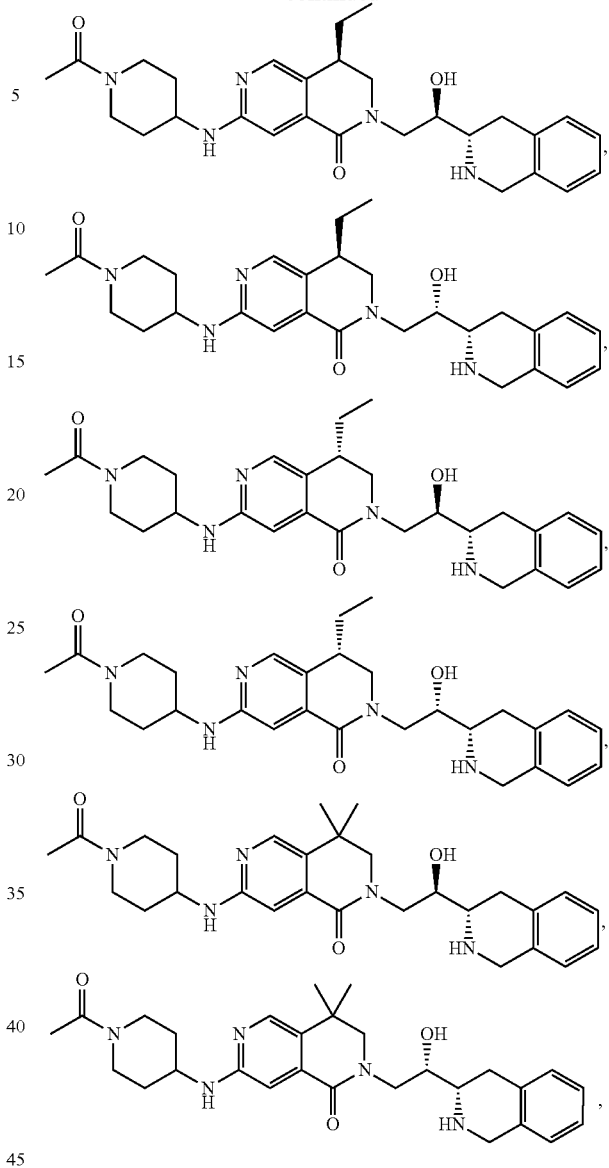
or a pharmaceutically acceptable salt thereof.
8. A composition for treating cancer comprising a compound of claim 2 and a pharmaceutically acceptable carrier.
9. A method for treating cancer comprising administering to a patient in need there of a composition of claim 8.
* * * * *